US005658570A

United States Patent [19]
Newman et al.

[11] Patent Number: 5,658,570
[45] Date of Patent: Aug. 19, 1997

[54] RECOMBINANT ANTIBODIES FOR HUMAN THERAPY

[75] Inventors: Roland A. Newman, San Diego; Nabil Hanna, Olivenhain; Ronald W. Raab, San Diego, all of Calif.

[73] Assignee: Idec Pharmaceuticals Corporation, San Diego, Calif.

[21] Appl. No.: 379,072

[22] Filed: Jan. 25, 1995

Related U.S. Application Data

[63] Continuation of Ser. No. 912,292, Jul. 10, 1992, abandoned, which is a continuation-in-part of Ser. No. 856,281, Mar. 23, 1992, abandoned, which is a continuation-in-part of Ser. No. 735,064, Jul. 25, 1991, abandoned.

[51] Int. Cl.$^6$ .......................... C07K 16/28; A61K 39/38; C12P 21/04
[52] U.S. Cl. ................... 424/184.1; 530/388.22; 435/70.21; 435/172.2; 435/172.3; 435/69.6; 935/96
[58] Field of Search ................... 424/184.1; 530/388.22; 435/69.6, 70.21, 172.2, 172.3; 935/96

[56] References Cited

U.S. PATENT DOCUMENTS

| 4,816,397 | 3/1989 | Boss et al. ............................. 435/68 |
| 4,816,567 | 3/1989 | Cabilly et al. ........................ 530/387.3 |
| 4,973,745 | 11/1990 | Schoemaker et al. ................ 530/387.3 |
| 4,975,369 | 12/1990 | Beavers et al. ........................ 435/69.5 |

FOREIGN PATENT DOCUMENTS

| 0451216 B1 | 10/1991 | European Pat. Off. . |
| 0 523 949 A1 | 1/1993 | European Pat. Off. . |
| 9008198 | 7/1990 | WIPO . |

OTHER PUBLICATIONS

Letvin, et al., Effect of Recombinant Soluble CD4 in Rhesus Monkeys Infected With Simian Immunodeficiency Virus of Macaques Abstract from the V Int. Conf. an AIDS, 1989, p. 535.
Watanabe, M. et al., *Proceedings of the National Academy of Sciences*, 88:4616–4620, (1991).
Rosenberg, M. et al., *Biotherapy*, "Soluble recombinant CD4—A potential therapeutic agent for HIV infector", 2:1107, (1990).
Riechmann, L. et al., *Nature*, "Reshaping human antibodies for therapy", 332:323–327, (1988).
Houghton, A.N. et al., *Seminars in Oncology*, "Monoclonal antibodies:potential applications to the treatment of cancer", 13:165, (1986).
Herpes Transformation, abstract 1985.
Amoroso et al., J. Immun., 145:3155, 1990.
Huse et al., Science, 246:1275, 1989.
BS Heteromycloma line, abstract 1986.
Ehrlich et al., Hum. Antibod. Hybridomas, 1990, vol. 1, No. 1.
Ehrlich et al., Hybridoma, vol. 6, No. 2, pp. 151–160, 1987.
Ehrlich et al., Hybridoma, vol. 7, No. 4, pp. 385–395, 1988.
Ehrlich et al., Clin. Chem., 34:1681, 1988.

Van Meel et al., J. Immunological Methods., 80:267, 1985.
Persson et al., Proc. Natl. Acad. Sci. USA, 88:2432, 1991.
Meek et al., J. Immun., 146:2434, 1991.
Allison et al., J. Immunological Methods, 95:157, 1986.
Nishimura, Y. et al., Cancer Research, 47:999 (1987).
Ward, E.S. et al., Nature, 341:544 (1989).
Camerini, D. and Seed, B., Abstract No. T.C.P. 125, V International Conference on AIDS, p. 587, (1989).
Camerini, D. and Seed, B., Cell, 60:747, (1990).
McClure, M.O. et al., Nature, 330:487, (1987).
Truneh, A. et al., Cell. Immun., 131:98 (1990).
Jones, P.T. et al., Nature, 321:522, (1986).
Harris et al. Tibtech vol. 11 p. 42, 1993.
Van Meurz et. al. Journal of Immunological Methods 95(1985) 123–128.
Morrison Science vol. 229. 1202, 1985 Immunology Today 10:253 (1989).
Queen et al. PNAS 8610029 (1989).
Waldmann Science vol. 252, 1657 1991.
Hird et. al. Genes and Cancer 1990 183.
Sharp, RM et al. 126 *J.Imm.Methods* 287 (1990) Feb. 4, 1994.
Ehrlich, PH et al. 28 *Mol.Immun.* 319 (1991) Feb. 4, 1994.
Groves, DJ & Tucker, EM 23 *Vet.Immuno. and Imunopath.1* (1989) Feb. 4, 1994.
Stanley, HA & Resse, RT 82 *PNAS* 6272 (1985) Feb. 4, 1994.
Schroeder et al. "Early Restriction of the Human Antibody Repertoire" Science, Nov. 6, 1987, vol. 238, pp. 791–793.
Combriato et al. "V Lambda and J Lambda–C Lambda Gene Segments of the Human Immunoglobulin Lambda Light Chain Locus are Separated by 14 KB and Rearrange by a Deletion Mechanism" European Journal of Immunology, Jun. 1991, vol. 21, pp. 1513–1522.
Hughes–Jones et al. "Nucleotide Sequences and Three–Dimensional Modelling of the VH and VL of Two Human Monoclonal Antibodies Specific for the D Antigen of the Human RH–Blood Group System" The Biochemical Journal, May 15, 1990, vol. 268, No. 1, pp. 135–140.
Stephens et al. "Antibodies are Produced to the Varible Regions of the External Envelope Glycoprotein of Human Immunodeficiency Virus Type 1 in Chimpanzees Infected with the Virus and Baboons Immunized with a Candidate Recombinant Vaccine" The Journal of General Virology, May 1992, vol. 73, No. 5, pp. 1099–1106.

*Primary Examiner*—Lila Feisee
*Attorney, Agent, or Firm*—Burns, Doane, Swecker & Mathis

[57] ABSTRACT

Chimeric antibodies including an Old World monkey portion and a human portion, nucleic acid encoding such antibodies, Old World monkey monoclonal antibodies, and methods for their production and use.

38 Claims, 26 Drawing Sheets

| | -20 | -19 | -18 | -17 | -16 | -15 | -14 | -13 | -12 | -11 | -10 | -9 | -8 | -7 | -6 | -5 | -4 | -3 | -2 | -1 | |
|---|---|---|---|---|---|---|---|---|---|---|---|---|---|---|---|---|---|---|---|---|---|

MONKEY

```
ATG GAC TGG ACC TGG AGG CTC CTC TTT ... GTG GTG GCA GCA GCT ACA GGT GCC AAG TCC   VH1
            TGT TCC ACG CTC CTG         TTG ... CTG CTG ACC GTC CCG TCC GTT TTG TCC   VH2
            TGT TCC ACA CTC TTG         TTG ... CTA CTG ACC GTC CCG TCC GTC TTG TCC    "
ATG GAG TTT GGG CTG AGC TGG GTT TTC ... CTT GTT GCT ATT TTC AAA GGT GTC TTG TCC   VH3
ATG GAG TTT GGG CTG AGC TGG GTT TTC ... CTT GTT GCT CTT TTA AAG GGC GTC CAG TGT    "
ATG GAG TTT GGG CTG AGC TGG GTT TTC ... CTT GTT GCT ATT TTA AGA GGC GTC CAG TGT    "
ATG AAA CAC CTG TGG TTC TTC CTC CTC ... CTG GTG GCG GCT CCC AGA GTC CTG TCC   VH4
ATG AAA CAC CTG TGG TTC TTC CTC CTC ... CTG CTG GCA GCT CCC AGA TGG GTC CTG TCC    "
                                        TG GCT GTT CTC CAA GGA GTC TGT TCC   VH5
```

HUMAN

```
ATG GAC TGG ACC TGG AGG GTC TTC TGC ... TTG CTG GCT GTA GCA CCA GGT GCC CAC TCC   VH1
ATG GAC TGG ACC TGG     ... ATC CTC TTC ... TTG GTG GCA GCA ACG GTC GTC CAC TCC    "
ATG GAC ATA CTT TGT TCC ACG CTC CTG ... CTA CTG ACT GTC CCG TCC GTC TTA TCC   VH2
ATG GAG ACT GGG CTG CGC TGG CTT TTT ... CTT GTG GCT ATT TTA AAA GGT GTC CAG TGT   VH3
ATG GAG TTT GGG CTG AGC TGG CTT TTT ... CTT GTT GCT ATT TTT AAA GGT GTC CAG TGT    "
ATG GAG CTT GGG CTG ACC TGG GTT TTC ... CTT GTT GCT CTT TTA AAA GGT GTC CAG TGT    "
ATG GAG CTT GGG CTG ACC TGG GTT TTC ... CTT GTT GCT CTT TTA GAT GTG AGG TCC TGT    "
ATG AAA CAC CTG TGG TTC TTC CTC CTC ... CTG TGT CAG CTC CCA GAT GTG AGG TCC TCC   VH4
ATG AAA CA.  CTG TGG TTC TTC CTT CTC ... CTG GTG GCA GCT CCC AGA TGG GTC CTG TCC    "
```

Underlined = Primer sequence

FIG. 1

5' 'Sense' Primers

A. Human or Monkey heavy chain early leader sequence primers with *Sal*I site $V_H1$     5' ACTAA<u>GTCGAC</u>ATGGACTGGACCTGG 3'

$V_H2$     5' ACTAA<u>GTCGAC</u>ATGGACATACTTTGTTCCAC 3'

$V_H3$     5' ACTAA<u>GTCGAC</u>ATGGAGTTTGGGCTGAGC 3'

$V_H4$     5' ACTAA<u>GTCGAC</u>ATGAAACACCTGTGGTTCTT 3'

$V_H5$     5' ACTAA<u>GTCGAC</u>ATGGGGTCAACCGCCATCCT 3'

$V_H6$     5' ACTAA<u>GTCGAC</u>ATGTCTGTCTCCTTCCTCAT 3'

B. Human or Monkey heavy chain late leader sequence primers with *Mlu* I site $V_H1$     5' G GCA GCA GC(CT) <u>ACG CGT</u> GCC CAC TCC GAG GT 3'   (+1 above ACG CGT)

$V_H2$     5' G ACC GTC CCG <u>ACG CGT</u> GT(TC) TTG TCC CAG GT 3'   (+1)

$V_H3$     5' GCT ATT TTC <u>ACG CGT</u> GTC CAG TGT GAG 3'   (+1)

$V_H4$     5' GCG GCT CCC <u>ACG CGT</u> GTC CTG TCC CAG 3'   (+1)

$V_H5$     5' G GCT GTT CTC <u>ACG CGT</u> GTC TGT GCC GAG GT 3'   (+1)

FIG. 7A

C. Human or Monkey framework 1 sequence primers with *Xho I* site $V_H1,3a,5$ CAGGTGCAGCTGCTCGAGTCTGG (+1)

$V_H2$ CAGGTCAACTTACTCGAGTCTGG (+1)

$V_H3b$ GAGGTGCAGCTGCTCGAGTCTGG (+1)

$V_H4$ CAGGTGCAGCTGCTCGAGTCGGG (+1)

$V_H6$ CAGGTACAGCTGCTCGAGTCAGG (+1)

3' 'Anti-Sense' Primers.

A. Human or Monkey Heavy Chain Constant Region Primers Anti-Sense Strand with *Nhe 1* site $IgG_{1-4}$ 5' GGC GGA TGC GCT AGC TGA GGA GAC GG 3' (+118 ... +110)

Nhe 1

FIG. 7B

5' 'Sense' Primers

A. Human or Monkey kappa light chain early leader primers with Bgl II site 1. 5' ATCAC<u>AGATCT</u>CTCACCATGGTGTTGCAGACCCAGGTC 3'

2. 5' ATCAC<u>AGATCT</u>CTCACCATGG(GA)G(AT)CCCC(TA)GC(TG)CAGCT 3'

3. 5' ATCAC<u>AGATCT</u>CTCACCATGGACATGAGGGTCCCCGCTCAG 3'

4. 5' ATCAC<u>AGATCT</u>CTCACCATGGACAC(GAC)AGGGCCCCCACTCAG 3'

B. Human or Monkey lambda light chain early leader primers with Bgl II site 1. 5' ATCAC<u>AGATCT</u>CTCACCATGGCCTGGGCTCTGCTGCTCC 3'

2. 5' ATCAC<u>AGATCT</u>CTCACCATGGCCTGGGCTCCACTACTTC 3'

3. 5' ATCAC<u>AGATCT</u>CTCACCATGACCTGCTCCCCTCTCCTCC 3'

4. 5' ATCAC<u>AGATCT</u>CTCACCATGGCCTGGACTCCTCTCTTTC 3'

5. 5' ATCAC<u>AGATCT</u>CTCACCATGACTTGGACCCCACTCCTC 3'

FIG. 7C

3' 'Anti-Sense' Primers

A. Human or Monkey kappa light chain constant region primer anti-sense strand with Kpn 1 and BsiW1 sites

$C_{kappa}$
```
          +108                                              +97
    5' CCG TTT GAT TTC CAG CTT GGT ACC TCC ACC GAA CGT 3'
                                 Kpn 1
          +112                                         +103
    5' TGC AGC ATC CGT ACG TTT GAT TTC CAG CTT 3'
                    BsiW1
```

B. Human or Monkey lambda light chain constant region primer anti-sense strand with Kpn 1, Hind III and Avr II sites

$C_{Lambda}$
```
       +107                                    +99
    5' ACC TAG GAC GGT AAG CTT GGT ACC TCC GCC 3'
                       Hind III    Kpn 1

+107                                                 +97
    5' ACC TAG GAC GGT CA(C/G) (C/G)TT GGT ACC TCC GCC GAA CAC 3'
                                    Kpn 1

+110                                   +102
    5' CTT GGG CTG ACC TAG GAC GGT CAG CCG 3'
                      Avr II
```

FIG. 7D

A. Heavy Chain Variable Region:

| VH1 | 5' | CCATGGACTGGACCTGG | 3' |
| VH2 | 5' | ATGGACATACTTTGTTCCAC | 3' |
| VH3 | 5' | CCATGGAGTTTGGGCTGAGC | 3' |
| VH4 | 5' | ATGAAACACCTGTGGTTCTT | 3' |
| VH5 | 5' | ATGGGGTCAACCGCCATCCT | 3' |
| VH6 | 5' | ATGTCTGTCTCCTTCCTCAT | 3' |

B. Heavy Chain Constant Region Anti-Sense Strand:

IgM    5'   +119        +115
              T TGG GGC GGA TGC ACT   3'

IgG$_{1-4}$  5'   +119        +115
              GA TGG GCC CTT GGT GGA   3'

C. Light Chain Variable Region:

Kappa  5'   +4                  +10
              G ATG ACC CAG TCT CCA (G/T)CC TC   3'

Lambda  5'   -9                  -3
              CTC A(C/T)T (T/C)(G/A)C TGC (A/C)CA GGG TCC   3'

D. Light Chain Constant Region Anti-Sense Strands:

Kappa  5'   +115        +110
              AA GAC AGA TGG TGC AGC CA   3'

Lambda  5'   +118        +112
              G GAA CAG AGT GAC CGA GGG G   3'

*FIG. 8*

```
                    S                                    Q
           A  KL    G                                    R   M
   Q       E  RI    T                                    K   V
XVQLVQSGAEVKKPGXSVXVSCKASGYTFS DYXIH WVRQAPGXGLEWXG
------------------------------FN-G NYAIS --------------
---Q--------------T-----------T    SYYIN --------V---S-

T
                       M        P
                    V  R  S    TS
                    I  LKA     FT
XINPSXGXTNYAPXFQG    RVTXTXDXSXNTAYMELSSLRSEDTAVYYCAR
WINTDTGNPTYAQGFKE    ---F-M---------KI-L K-----------
WINPSNGNTGYAQKFQG    -----------------N-----------

V                        Homology
                          G
XYGFYSNDYXXXXXXYTXDY  WGQGTLVTVSS   Human VH1 consensus
VVGTTYAEYFEF          ----A------   Monkey clone 1-2    88%
MYSWKGT          FDY  -----------   Monkey clone 1-14   94%
```

FIG. 9A

```
                    G
      Q             A                                        I                         G
      K             T         Q                  F           F                         A
XVTLRESGPXLVKPTETLTLTCTVSGFSLS  TXGMXVG   WIRQPPGKXLEWLA
------------------------------  TSGTGYS   ---------------
------------------------------  ASGTGVA   ----S--------T
------------------------------  TSETGVG   ---------------

TM        A
                                      RLTNM     V
                                      NVSSV     G
RINXWDDDKYYSTSLRS    RLTISKDTSKNQVVLXXXXXXDPXDTATYYCAR
RID WDNDRYYSTSLKN    -----------------------L----------
SIF WTGVKYYNTSLKN    -----S----D----A------I-------G-
SIY WNDVKYYITFLKS    -----R----------------------------

Homology
                     L
RXPRXXXGDXGXYXXAFDV  WGQGTTVTVSS      Human   VH2 consensus
GGSI                 DY       ----V------     Monkey  clone 2-3    98%
GVYWSGYS             FDY      ----A------     Monkey  clone 2-13   91%
IPGTAGTVPYYTL        DS       ----AV-----     Monkey  clone 2-10   97%
```

FIG. 9B

```
                                              G
         I              S       N             S
         A              V       S             A
EVQLVESGGGLVQPGGSLRLSCAASGFTFS  DYAMH  WVRQAPGKGLEWVX
----E--------F----------------  TYDMT  --------------
------------------------------  EYSIH  -----Q----R---
------------------------------  SYDMN  --------------
---------------S--------------  NYNMD  ----S---------

MV      S   KT
                          NA      SAF  D  EP     L  F   T
HIEEKXNGSATYYADSVKG       RFTISRDDSKNTLYLQMNSLRAEDTAVYYCAR
RISW  NSGTIYYASSVKG       ----------------------R--------
LAGKKADRYKTEYATAVKG       -------------S------T----------
YISS  ASGYIYYADSVKG       -------F------S----------------
RVIRK GARTKYAASVKG        -------------------------------

Homology

DPEVESLXXXFXYXXFFDS  WGQGTLVTVSS   Human VH3 consensus
GTALCSDSGCSS    DV   -----------   Monkey clone 3-34  96%
PVLGDRWF       FDL   -----PI----   Monkey clone 3-36  93%
GQPVLQFLEWLLPTTGSDV  --P-V------   Monkey clone 3-40  95%
DVAAAGT              G---V------   Monkey clone 3-9   95%
```

FIG. 9C

```
                              T   Y V                    S   R
QVQLQESGPGLVKPSETLSLTCAVSGGSIS SSYYWS WIRQPPGKGLEWIG
-M--------------------------- SSYDWT -------M-----A
----------------------------- SGYYWG ----T--------
--H-------------------S------ SSGYYWG -------------
-----------------------------  GYYWG ----T--------
------A---------------S------ GDYYWF -------------

M P KK  H Y    N
YIYY  SGSTYYNPSL KSRVTISVDTSKNQFSLKLSSVTAADTAVYYCAR
VISGN SGSADYNPSL -N---------N------MT---------I-----
SLQGR GGNKYLNLCL -----L-A-------------------------
SIHGS GGSNSLNPSL -----L------G-K---------------F---
SLQGR GGNKYLNLSL -----L-A-------------------------
YIYGS GGGTNYNPSL NN--S--I-----L-----R------------S
```

```
                                                     Homology
..................         Human  VH4   consensus
GDVTSGWYRGY    FDS  WGQGCLVTVSSG Monkey clone 4-13    90%
VGDNR          FDV  WGPGVLVTVSSG Monkey clone 4-14    96%
ELYSSSPY       YFDF WGQGVRVTVSSG Monkey clone 4-16    92%
GDNR           FDV  WGPGVLVTVSS  Monkey clone SC CHIM 96%
NILKYLHWLLY         WGQGVLVTVSS  Monkey anti-CD4 CHIM 88%
```

FIG. 9D

```
                       R
EVQLVQSGAEVKKPGESLKISCKGSGYSF  TSYWIG   WVRQMPGKGLEW
--------G---R-----R----TC-F--  TGFWIS   ----V--Q----

MGIIYPGDSDTRYSPSFQGH  VTISADKSISTAYLQWSSLKASDTAMYYCAR..
VGRVSPGDSITRYNPSFQGH  ---------T-TF---N--------------Q

Homology
..........      ...  .............     Human  VH5  consensus
RAGNGNYYQD      FYY  WGHGVLVTVSSG      Monkey clone 5-11    84%
```

FIG. 9E

```
                              V
DIQMTQSPSSLSASVGDRVTITC  RASQSVXXSDISSYLN  WYQQKP
DIQMTQSPAS-------K-----  RASQ    SFSSSLA   ------
DIQMTQSPAS-------------  QASQ    SVSNLLA   ------
DIQMTQSPAS----------V--  RASQ    GINQELS   ------
DIQMTQSPAS-------------  RASQ    GISSYLN   ------

R
                              G          I
GKAPKLLIYXASSLES  GVPSRFSGSGSGTDFTLTISSLQPEDFATYYC
--------DSASSLQS  ---------K------------------S---
-----P---KASSLES  ------TR----------N--E-------F-
----T----AASSLQT  ------------------S--PE---V--ED-
---------L
```

```
                                                   Homology
QQYNSLPXXYD  YT  FGQGTKVEIK    Human   VK1  consensus
QQYYSYPR     LT  ----------    Monkey  clone K1-7   94%
QQGNSYP      LT  --G-------    Monkey  clone K1-3   90%
LQDYMSP      WT  ----------    Monkey  clone K1-14  90%
```

*FIG. 9F*

```
                                        R
DIVMTQSPLSLPVTPGEPASISC  RSSQSLVHSNGNTYLN  WYLQKP
DIVMTQSPAS----L-G------  TSTQSLLSGNGYSYLN  ------
-LA-P---A--A----Q------  RASESV SFFGVNLIH  ------

GQSPQLLIY  KVSNRFS  GVPDRFSGSGSGTDFTLKISRVEAEDVGVYYC
----H----  YDSYRAS  ---T---------------------------
--P------  QASNKDT  ---A--------------FNP---D-A-D---

V
           L  R                              Homology
MQALQSP YT  FGQGTKNEIK      Human  VK2 consensus
MQTLQSP FT  --P----D--      Monkey clone K2-8   91%
LQSKNSPR T  --G-------      Monkey SC CHIM      81%
```

FIG. 9G

```
                               S
SYELTQPPSVSVSPGQTARITC  SGDALGQKYVY  WYQQKP
----S--R-----------GF-- GGDNVGRKSVQ  ------

M
                                              G
                                    T         G
                            N       AQ        E
GQAPVLVIY  EDSKRPS  GIPERFSGSNSGTTATLTISGVEAXDEADYYC
P--------  ADSERPS  ---A------------------------------

QAWDSXTXXVV  FGGGTKLTVLG      Human λ III  consensus
QVWDSTADHWV  -----R-----      Monkey Anti-CD4   91%
```

*FIG. 9H*

```
                                   S                            G
                 I                 V                            S
                                                                A
EVQLVESGGGLVQPGGSLRLSCAASGFTFS    DYAMH    WVRQAPGKGLEWVX
Q-----------V----R-----------     SYGMH    --------------
Q-----------V-G--R---------S--    SYGMH    ----C---------
Q-----------V---SR------------    SYAMH    ---G----------
----L-------------------V---N--   SCTMT    --------------
------------------R---------N-G   DYSMT    --------------
------------------R------------   SYAMS    --------------
--R------D--E------V--EV---I--    KAWMN    ----------Q---
-M-------AF-------K----------N--  DSTIH    -----S--S-----
-------------------------------   SYDMN    --------------
------------A------S---V-------   NYNMD    ----S---------
----E--------F-----------------   TYDMT    --------------
------------------------------S-- EYSIH    -----Q----R---
X-T-R---PX--K-TET-T-T-TV---SL-    TXGMXVG  -I--P---X---L-

MV    S  KT
                                       NA SAF   D  EP    L F  T
HIEEKXNGSATYYADSVKG   RFTISRDDSKNTLYLQMNSLRAEDTAVYYCAR
VIS    YDGSNEYFADSVKG ---------N----MG-----------------
VIS    DDGSNKYYADSVKG ----------K----------D---------K
VIS    YDGSNKYYADSVKG --------------S-----------------
TIS    ASGYATYYADSVKG -I-------------------A-------N
SIRSKDYGGTTEYAASVKG   -----------SI-------------------S-
AISG   SGGSTYYADSVKG  --------------------------------K
QIKNKVDGGTIDYAAPVKG   --I-----S---------KI--------VG
HIENKTKNYATIYRASVKG   ------------AF---D---PD---L----P
YIS    SASGYIYYADSVKG -------FA--S-S---S--------------
RVI    RKGARTKYAASVKG --------------S--KT-----------
RIS    WNSGTIYYASSVKG -------------------R-----------
LAGKKADRYKTEYATAVKG   ----------S-------T------------
RIN    XWDDDKYYSTSLRS -L---K-T---QVV-XXXXXDPX---T-----

DPEVESLXXXFXYXX  FFDS  WGQGTLVTVSS    Hum VH3
DRVAVYASVFFID    SFDI  -----G--       RF TS2      92%
GVYCSSSSCYSYYYYHYMDV   --K--T--       RF SJ1      87%
GRFCSGQSCYSYYYYYYMDV   -K--T-----     RF SJ2      91%
NISETL           DS    ----------     BE          93%
NNTSPY           FDY   --E--------    CHERRI      92%
GQVLYYGSGSYHW    FDP   -----------    18/2        98%
NYTGTV           DY    ----------     K6H6        84%
PPEVESLRS              --R--------    1B11        83%
GQPVLQFLEWLLPTTGS DV   --P-V------    monkey #40  92%
DVAAAGT                G---V------    monkey #9   90%
GTALCSDSGCSS     DV    ----------     monkey #34  95%
PVLGDRWFF        DL    -----PI-I--    monkey #36  91%
RXPRXXXGDXGXYXXA FDV   -----T-----    Hum VH2     60%
```

FIG. 10

```
        M   K   H   L   W   F   F   L   L   L   V   A   A   P   R
       GAC ATG AAA CAC CTG TGG TTC TTC CTC CTC CTG GTG GCA GCC CCC AGA

+1                                      10
        W   V   L   S   Q   V   Q   L   Q   E   A   G   P   G   L   V
       TGG GTC TTG TCC CAG GTG CAG CTG CAG GAG GCG GGC CCA GGA CTG GTG

20
        K   P   S   E   T   L   S   L   T   C   S   V   S   G   G   S
       AAG CCT TCG GAG ACC CTG TCC CTC ACC TGC AGT GTC TCT GGT GGC TCC 30                                          40
        I   S   G   D   Y   Y   W   F   W   I   R   Q   S   P   G   K
       ATC AGC GGT GAC TAT TAT TGG TTC TGG ATC CGC CAG TCC CCA GGG AAG 50                                          60
        G   L   E   W   I   G   Y   I   Y   G   S   G   G   G   T   N
       GGA CTG GAG TGG ATC GGC TAC ATC TAT GGC AGT GGT GGG GGC ACC AAT

70
        Y   N   P   S   L   N   N   R   V   S   I   S   I   D   T   S
       TAC AAT CCC TCC CTC AAC AAT CGA GTC TCC ATT TCA ATA GAC ACG TCC 80                                      90
        K   N   L   F   S   L   K   L   R   S   V   T   A   A   D   T
       AAG AAC CTC TTC TCC CTG AAA CTG AGG TCT GTG ACC GCC GCG GAC ACG

100
        A   V   Y   Y   C   A   S   N   I   L   K   Y   L   H   W   L
       GCC GTC TAT TAC TGT GCG AGT AAT ATA TTG AAA TAT CTT CAC TGG TTA 110                                         120
        L   Y   W   G   Q   G   V   L   V   T   S   S
       TTA TAC TGG GGC CAG GGA GTC CTG GTC ACC GTC TCC
```

FIG. 13

```
         M   A   W   A   L   L   L   L   G   L   L   A   H   F   T
ACC ATG GCC TGG GCT CTG CTG CTC CTC GGC CTC CTT GCT CAC TTT ACA

+1                                          10
 D   S   A   A   S   Y   E   L   S   Q   P   R   S   V   S   V
GAC TCT GCG GCC TCC TAT GAG TTG AGT CAG CCT CGC TCA GTG TCC GTG

20
 S   P   G   Q   T   A   G   F   T   C   G   G   D   N   V   G
TCC CCA GGA CAG ACG GCC GGG TTC ACC TGT GGG GGA GAC AAC GTT GGA 30                                      40
 R   K   S   V   Q   W   Y   Q   Q   K   P   P   Q   A   P   V
AGG AAA AGT GTA CAG TGG TAC CAG CAG AAG CCA CCG CAG GCC CCT GTG 50                                      60
 L   V   I   Y   A   D   S   E   R   P   S   G   I   P   A   R
CTG GTC ATC TAT GCT GAC AGC GAA CGG CCC TCA GGG ATC CCT GCG CGA

70
 F   S   G   S   N   S   G   N   T   A   T   L   T   I   S   G
TTC TCT GGC TCC AAC TCA GGG AAC ACC GCC ACC CTG ACC ATC AGC GGG 80                                      90
 V   E   A   G   D   E   A   D   Y   Y   C   Q   V   W   D   S
GTC GAG GCC GGG GAT GAG GCT GAC TAT TAC TGT CAG GTG TGG GAC AGT

100
 T   A   D   H   W   V   F   G   G   G   T   R   L   T   V   L
ACT GCT GAT CAT TGG GTC TTC GGC GGA GGG ACC CGG CTG ACC GTC CTA

109
 G
GGT
```

FIG. 14

RECOMBINANT ANTIBODIES FOR HUMAN THERAPY

This application is a continuation of application Ser. No. 07/912,292, filed Jul. 10, 1992 now abandoned, which is a continuation-in-part of Ser. No. 07/856,281, filed Mar. 23, 1992 now abandoned, which is a continuation-in-part of Ser. No. 07/735,064, filed Jul. 25, 1991 now abandoned.

FIELD OF THE INVENTION

The whole of which, including drawings, are both hereby incorporated by reference. This invention relates to recombinant antibodies useful for human therapy, and to methods for production of such antibodies.

BACKGROUND OF THE INVENTION

Murine monoclonal antibodies are used in diagnosis of human disease, and in solving basic biological research problems. These reagents are also used in clinical trials as therapeutics for both acute and chronic human diseases, including leukemias, lymphomas, solid tumors (e.g., colon, breast, hepatic), AIDS and autoimmune diseases.

Mouse/human chimeric antibodies have been created, and shown to exhibit the binding characteristics of the parental mouse antibody, and effector functions associated with the human constant region. See e.g., Cabilly et al., U.S. Pat. No. 4,816,567; Shoemaker et al., U.S. Pat. No. 4,978,745; Beavers et al., U.S. Pat. No. 4,975,369; and Boss et al., U.S. Pat. No. 4,816,397 all of which are incorporated by reference herein. Generally, these chimeric antibodies are constructed by preparing a genomic gene library from DNA extracted from pre-existing murine hybridomas. Nishimura et al., 47 *Cancer Research* 999, 1987. The library is then screened for variable region genes from both heavy and light chains exhibiting the correct antibody fragment rearrangement patterns. The cloned variable region genes are then ligated into an expression vector containing cloned cassettes of the appropriate heavy or light chain human constant region gene. The chimeric genes are then expressed in a cell line of choice, usually a murine myeloma line.

Such chimeric antibodies have been used in human therapy. Antibodies to these chimeric antibodies, however, have been produced by the human recipient in a number of cases. Such anti-chimeric antibody antibodies are detrimental to continued therapy with the chimeric antibody.

Erlich et al., 34 *Clinical Chemistry* 1681, 1988, Erlich et al., 7 *Hybridoma* 385, 1988, Erlich et al., 6 *Hybridoma* 151, 1987, and Erlich et al., 1 *Human Antibody Hybridomas* 23, 1990 (not admitted to be prior art to the present application) state that human monoclonal antibodies are expected to be an improvement over mouse monoclonal antibodies for in vivo human therapy. They also postulate that non-human primate antibodies, e.g., chimpanzee monoclonal antibodies, to be tolerated in humans because they are structurally similar to human antibodies. Because human antibodies are non-immunogenic in Rhesus monkeys (i.e., do not induce an antibody response), they predict that primate antibodies will be non-immunogenic in humans. They indicate that the testing of antibodies in humans is unnecessary if a primate antibody has a constant region structure identical to that of a human immunoglobulin or, at least, a structure no more different from a human immunoglobulin than the different human antibodies differ from each other. Thus, they suggest that chimpanzee antibodies may be useful in human therapy.

SUMMARY OF THE INVENTION

The present invention concerns methods for the amplification and cloning of Old World monkey (referred to herein as "monkey," e.g., baboon or macaque) antigen-binding portions of immunoglobulin variable region-encoding genes, the fusion of these genes to cloned human, chimpanzee or other monkey constant region-encoding genes (and human, chimpanzee or other monkey framework-encoding genes if required), and their expression as human/monkey recombinant antibodies, or wholly monkey recombinant antibodies. Furthermore, the invention concerns use of such recombinant antibodies (which term includes antibodies produced by fusion of DNA from two different antibody genes, even from the same species, e.g., two different monkey antibody genes, for example, Rhesus and cynomolgus monkeys, to give a monkey-monkey recombinant antibody) as immunotherapeutic agents for the treatment of human disease. The invention is based upon the discovery that evolutionary distant monkeys (e.g., baboon or macaque monkeys (including cynomologus, and Rhesus monkeys)), unlike the Chimpanzee, are not only sufficiently different from humans to allow antibodies against human antigens to be raised in these monkeys, even to relatively conserved human antigens, e.g., CD4 and CD54, but are sufficiently similar to humans to have antibodies similar to human antibodies, so that there is no host anti-antibody immune response when such monkey antibodies, or recombinant antibodies derived therefrom, are introduced into a human.

Unlike some prior antibodies used for human therapy, the antibodies of the present invention do not suffer from several drawbacks, e.g., 1) immunogenicity and induction of human anti-antibody (HAA) response upon repeated administration necessary to treat chronic conditions, 2) relatively short half-life compared to human antibodies, and 3) lack of effector functions with human cells or complement. The lack of these drawbacks is a significant advantage for human therapy with antibodies made by the present invention. For example, in the case of chronic human diseases, including auto-immune diseases, or any disease where prolonged administration of an antibody is necessary, one of the major obstacles to repetitive antibody therapy is the host response to the therapeutic antibody. HAA responses are often unpredictable from one patient to another. Such responses are predominantly, though not exclusively, directed against the constant region of the antibody molecule, and once they occur they often preclude, or reduce the effectiveness of, any further therapy with that antibody, or another antibody of the same isotype.

Potentially, the problems of HAA could be circumvented by the use of human monoclonal antibodies. This approach, however, suffers from the ethical, clinical, and immunological limitations on immunization of human subjects with many antigens of choice (e.g., human antigens, which phrase includes antigenic or immunogenic portions of any proteins, polypeptides or their equivalent present in a human) for antibody generation. The inventors' approach to circumvent this problem includes generation of antibodies of the appropriate specificity and desired effector function, and their use in production of recombinant antibodies. These recombinant antibodies generally include an appropriate portion of the variable region of an antibody derived from an immunized monkey, and the constant region of an antibody from a human or chimpanzee. Thus, the specificities and high affinities of monoclonal antibodies are retained, and the appropriate human or chimpanzee constant region displaying the desired effector functions can be readily chosen.

The present invention is further based on a method for amplification of monkey immunoglobulin genes, e.g., by the polymerase chain reaction (PCR), from RNA extracted from monkey lymphocytes using synthetic oligonucleotide primers specific for heavy and light chain variable region gene families. The amplified genes or appropriate portions (e.g., complementarity determining region (CDR)-coding regions; see Winter, British Patent Application No. GB2188638A, hereby incorporated by reference herein) are cloned into an expression vector containing a human or chimpanzee constant region gene for the production of a monkey/human recombinant antibody, or a vector containing a monkey constant region gene for the production of wholly monkey recombinant antibody of the desired isotype. These antibodies represent immunotherapeutic agents capable of localizing and/or killing appropriate target cells (e.g., tumor cells) after in vivo administration.

Thus, in a first aspect the invention features a method for cloning an antigen-recognizing portion of the variable region of a monkey antibody gene. This method includes providing nucleic acid, e.g., RNA from the monkey, forming cDNA to the RNA (using reverse transcriptase), providing a primer complementary to the cDNA sequence encoding a 5' leader sequence of the antibody gene, contacting that cDNA and the primer to form a hybrid complex and amplifying the cDNA to produce nucleic acid encoding the variable region of the monkey antibody gene.

By "antigen-recognizing portion" is meant one or more portions of a variable region of a monkey antibody which are responsible for binding and/or recognizing the target antigen (or epitope or idiotype) of the antibody. For example, it includes the CDR regions (see below) or the whole variable region, or any combination of these two regions including any changes in coding regions that may be induced to make the region more human-like rather than monkey-like, without altering the specific binding properties of the antibody. If only a portion of the whole variable region is used then the remaining portions, e.g., the so-called "framework", are provided from another antibody, preferably a human or chimpanzee antibody (see below) and in the art cited above and incorporated herein by reference.

The phrases "variable region", "leader sequence", "constant region" and "framework" are used in their common art recognized manner, examples of which are provided below and in the art cited above and incorporated herein by reference.

In preferred embodiments, the leader sequence is a human, chimpanzee or monkey leader sequence of approximately 60 bases, examples of which are provided in FIG. 1.

The inventors have discovered that the monkey, chimpanzee and human variable region leader sequences are sufficiently similar that primers constructed to one are suitable for amplification of the other. In the method, the RNA is amplified sufficiently to produce enough nucleic acid to place that nucleic acid within a vector for later cloning.

In a second aspect, the invention features a method for producing an antibody to a human antigen, which antibody is not immunogenic in humans. The method involves raising in a monkey a monkey antibody to the human antigen, and isolating monkey nucleic acid encoding an antigen-recognizing portion of a variable region of the monkey antibody. Human nucleic acid encoding a human constant region of an antibody is provided, and ligated to the monkey nucleic acid to form recombinant nucleic acid. This recombinant nucleic acid is then expressed to produce the desired antibody. Alternatively, chimpanzee or monkey constant region-encoding nucleic acid can be used to form the recombinant antibody. There are few, if any, differences in the amino acid sequence of human and chimpanzee constant regions (i.e., they are homologous), and those differences present between human and monkey can be readily altered by standard techniques if the nucleic acid encoding the monkey constant region is used to form a recombinant antibody. All that is critical in the invention is that an antibody be produced that is less immunogenic than the monkey constant region so that no significant immune response ensues when the recombinant antibody is introduced into a human. (Such antibody regions are herein referred to as homologous regions.) Thus, the recombinant antibody is engineered to be functionally the same as a human antibody in its amino acid sequence, i.e., it has a constant region homologous to a human or chimpanzee antibody constant region. In summary, the antibody is as human an antibody as is necessary to reduce the chance of an undesired immunological response to the antibody, and contains an antigen-binding portion of a monkey antibody.

By "not immunogenic" is meant that the antibody does not raise an antibody response of sufficient magnitude to reduce the effectiveness of continued administration of the antibody in the majority of humans for sufficient time to achieve therapeutic efficacy, e.g., as compared to a murine or murine-human chimeric antibody. Preferably, no antibody response is observed.

In preferred embodiments, the method includes immortalizing a cell of the monkey which is responsible for producing the monkey antibody, e.g., by hybridoma fusion, viral transformation with *Herpes papio*, single B-cell cloning (also termed "transient immortalization"), and production of a library of recombinant immunoglobulins. In other preferred embodiments, the method includes selecting a B-cell from the monkey from either a peripheral blood leukocyte, the spleen, bone marrow or a lymph node; selecting a clone which produces the appropriate antibody; rescuing the immunoglobulin genes encoding that antibody from the immortalized cell line; and reexpressing the genes in a producer cell line (i.e., a cell line which causes sufficient production of the antibody to be useful for human therapy).

In a third aspect, the invention features a recombinant antibody formed from either a human or chimpanzee constant region and an antigen recognizing portion of a monkey variable region, or a first monkey constant region and a second, different monkey antigen recognizing portion of a variable region.

In a related aspect, the invention features a monoclonal antibody, or an Fab, (Fab)$_2$, a light chain or heavy chain dimer, or any minimal recombinant fragment thereof, such as an Fv or a SCA (single chain antibody) or other immunologically active fragment thereof (e.g., a CDR-region), to a human antigen formed by an immortalized monkey B-cell. Such fragments are useful as immunosuppressive agents. Alternatively, the antibody of the invention may have attached to it an effector or reporter molecule. For instance, an antibody of the invention may have a macrocycle, for chelating a heavy metal atom, or a toxin, such as ricin, attached to it by a covalent bridging structure. In addition, the Fc fragment or CH3 domain of a complete antibody molecule may be replaced by an enzyme or toxin molecule, and a part of the immunoglobulin chain may be bonded with a polypeptide effector or reporter molecule. Bispecific antibodies can also be constructed by standard procedure.

In another aspect, the invention features pharmaceutical compositions in which antibodies of the present invention are provided for therapeutic or prophylactic uses. Such antibodies can also be provided as immunotoxins, i.e., molecules which are characterized by two components and are particularly useful for killing selected cells in vitro or in vivo. One component is a cytotoxic agent which is usually fatal to a cell when attached or absorbed. The second component, known as the "delivery vehicle" provides a means for delivering the toxic agent to a particular cell type, such as carcinoma cells. The two components are commonly chemically bonded together by any of a variety of well-known chemical or genetic procedures. For example, when the cytotoxic agent is a protein and the second component is an intact immunoglobulin, the linkage may be by way of heterobifunctional crosslinkers, e.g., carbodiimide, glutaraldehyde, and the like. Production of various immunotoxins is well-known in the art.

In another related aspect, the invention features nucleic acid encoding a human/monkey recombinant antibody. In preferred embodiments, the nucleic acid encodes a human or chimpanzee constant region and an antigen recognizing portion of monkey variable region; and the nucleic acid is purified, i.e., separated from biological components with which it naturally occurs, or more preferably, is provided as a homogeneous solution.

In yet another aspect, the invention features a CDR-grafted antibody formed from at least one of the complementarity determining regions (CDRs), that is, amino acid residues (using the standard amino acid labeling system of Kabat) 31–35 (CDR 1), 50–65 (CDR 2) and 95–102 (CDR 3) of the specified heavy chain, and amino acid residues 24–34 (CDR 1), 50–56 (CDR 2) and 89–97 (CDR 3) of the specified light chain of an Old World monkey variable region, and an immunoglobulin variable region framework from a second species. The CDR-grafted antibody is able to bind to the same antigen as the original monkey antibody. The antibody constant region is derived from a human or chimpanzee immunoglobulin. The methodology for performing this aspect is generally described by Jones et al., 321 *Nature* 522, 1986. Such CDR grafts can be altered if desired to ensure that they appear more human-like so that the probability of instigation of adverse reaction to the antibody is lessened.

In preferred embodiments, the method includes immortalization or selection of a cell from a macaque, which is responsible for producing a macaque antibody, and rescuing the immunoglobulin genes from the cell; cloning and sequencing the antibody genes responsible for the production of antibody; selecting a human variable region framework sequence (preferably with the closest homology to the macaque variable region framework); and substituting macaque CDR sequences for human CDR sequences and minor modifications in the human framework region may be included to maintain affinity of the antibody for its antigen.

By "minor modifications" is meant that less than a total of about 6 amino acids in the framework may be substituted by other amino acids. Usually such substitutions or modifications are made only when those amino acids are involved in conformational interactions that hold the framework in an appropriate form so that the desired antigen is recognized by the antibody. Such modifications will generally reflect those differing amino acids present in a monkey antibody, compared to a human antibody. For example, the amino acid sequence of a human antibody just prior to heavy chain CDR 3, 92–94 is generally cysteine-alanine-arginine (arginine is known to be replaced in a minority of antibodies with serine or threonine); in some antibodies in the monkey the sequence is cysteine-alanine-serine; thus, in this example, it may be preferred to use serine at amino acid 94 (see FIG. 9D).

In a further aspect, the invention features a method for treating a human having a particular antigen, e.g., one associated with disease. The method includes administering a therapeutically effective amount of a recombinant antibody specific for the particular antigen, wherein the recombinant antibody is one having either a human or chimpanzee constant region and an antigen recognizing portion of a monkey variable region, or a first monkey constant region and an antigen-recognizing portion of a second, different monkey variable region.

In preferred embodiments of the above aspects, the antigen is a tumor antigen, an antigen involved in an immune disorder, an antigen involved in an autoimmune response, a receptor expressed on a host cell, or an antigen selected from the human antigens CD58, VLA4 ($\alpha 4\beta 1$ integrin), CD2, LFA3, ELAM, LAM, CD25, CD4, CD19, CD20, human T-cell receptor, CD3, CD8, CD23, CD41, CD44, CD45, CD71, TNF$\alpha$, TNF$\beta$, Tn antigen, IL-1, IL-8, C5a, adhesion molecules, e.g., VCAM, CD54, CD28, CD11a, CD11c, CD18, and CD11b, the neu oncogene product, MDR-1 (P-glycoprotein), TGF$\alpha$ and its receptor, and PDGF; and the recombinant antibody is active to either deplete (kill or eliminate) undesired cells (e.g., anti-CD4) by acting with complement, or killer cells, or is active as a cytotoxic agent or to cause Fc-receptor binding by a phagocyte. Alternatively, the antibody blocks or stimulates receptor functions, or neutralizes active soluble products, such as one or more of the interleukins, TNF and C5a.

In other aspects, the invention features pharmaceutical compositions of the above antibodies or fragments thereof. Compositions or products according to the invention may conveniently be provided in the form of solutions suitable for parenteral or nasal or oral administration. Appropriate preparations of antibody may be mixed with appropriate preparations of other agents, resulting in increased clinical utility.

Other features and advantages of the invention will be apparent from the following description of the preferred embodiments thereof, and from the claims.

DESCRIPTION OF THE PREFERRED EMBODIMENTS

The drawings will first briefly be described.

BRIEF DESCRIPTION OF THE DRAWINGS

FIG. 1 is a tabular representation of 20 codons in nine different Ig heavy chain leader sequences and ten monkey Ig heavy chain leader sequences;

FIGS. 7A–7D, and 8 show the nucleic acid sequence of various leader sequence primers useful in the invention (these primers in FIG. 8 correspond to those listed as SEQ. ID Nos. 1–12 infra;

FIGS. 9A through 9H are comparisons of human and monkey regions in the VH1, VH2, VH3, VH4, and VH5 sequences, and VKI and VKII, and VlambdaIII sequences, respectively;

FIG. 10 is a comparison of human and monkey VH3 sequences, with one comparison to the human VH2 sequence;

FIGS. 13 and 14 are portions of the nucleotide sequences of anti-CD4 VH, and VL regions respectively;

Monkey Antibodies

Old World monkeys include those referred to as baboon and macaque monkeys (including Rhesus monkey and cynomolgus monkey). This invention provides details of use of the claimed invention with various monkey genes. These examples are not limiting in the invention and may be readily applied to other Old World Monkeys.

Figure 2:
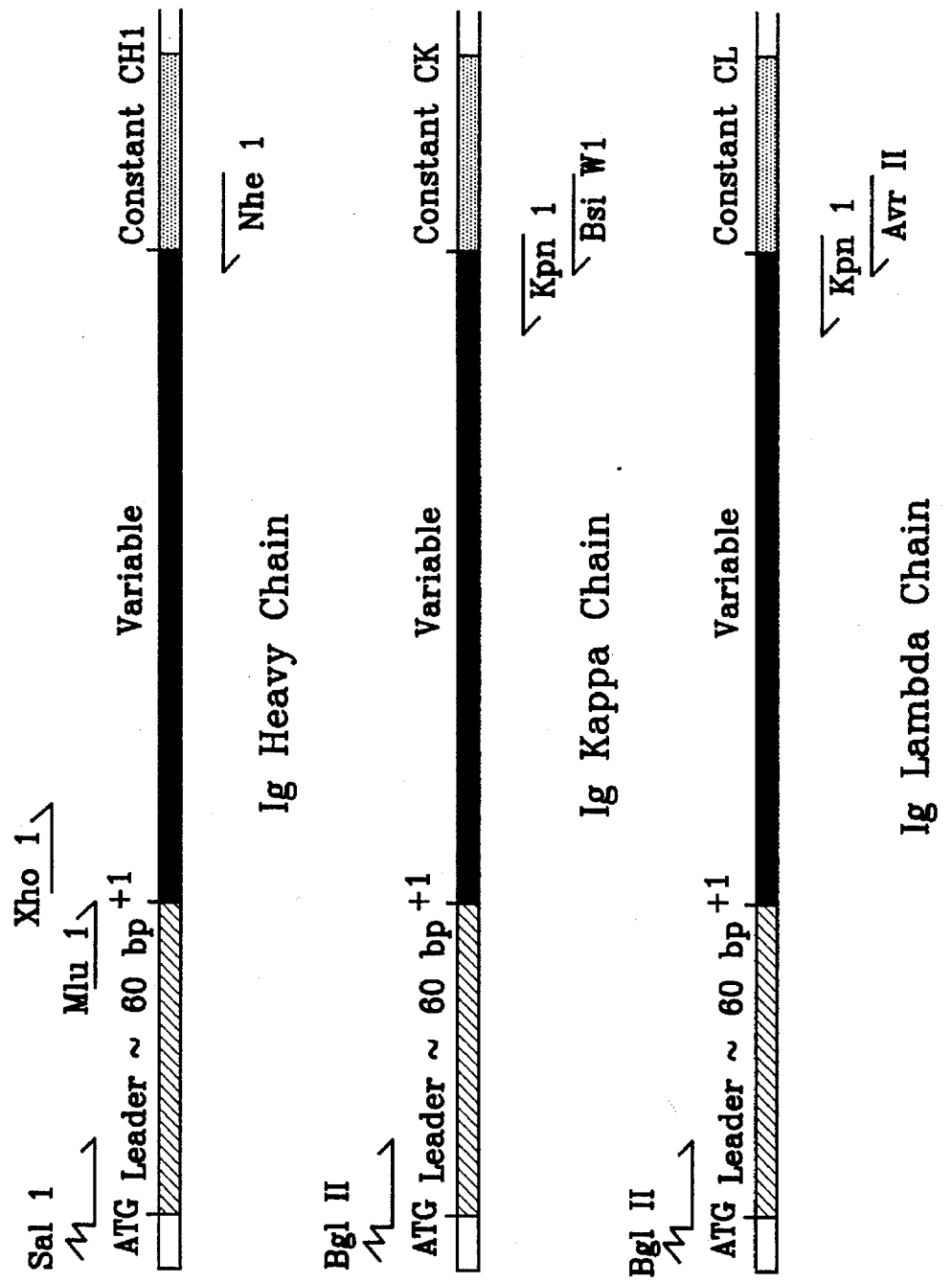
FIG. 2 is a diagrammatic representation of the structure of various Ig chains showing the relative position of leader, variable, and constant regions with the positions of restriction sites and primers used for amplification.

Referring to FIG. 2, there is shown in diagrammatic form the general structure of genes encoding immunoglobulin heavy, kappa light, and lambda light chains. Each of these chains is formed with an ATG start codon followed by a leader sequence of approximately 60 bases, a region encoding a variable region of the immunoglobulin, and a constant region of that immunoglobulin. Examples of different leader sequences, or signal peptides, of heavy chains are shown in FIG. 1. These sequences, and their equivalent in monkey, can be determined by standard techniques well known to those of ordinary skill in the art, and as described below.

The sequences shown in the lower portion of FIG. 1 are human leader sequences. The inventors have discovered that construction of primers complementary to these leader regions allows amplification of Ig genes from monkeys. Similarly, primers homologous to monkey leader sequences (see e.g., upper portion of FIG. 1) can be used in amplification of monkey immunoglobulin genes, and also for amplification of human immunoglobulin genes.

By use of such primers in standard amplification procedures, genes encoding various monkey immunoglobulin genes, can be readily isolated, and the sequences encoding the variable regions of the antibodies determined. Examples of such procedures are provided below. The results of the analysis provided below are presented in FIGS. 9A through 9H, and in FIG. 10. Surprisingly, the inventors found that, despite the ability to produce antibodies to relatively conserved human antigens in the monkeys, the variable regional framework sequences of the antibodies so produced were indistinguishable from those of human antibodies. That is, the amount of variability in immunoglobulin sequence observed for the monkeys was similar to that observed for humans, and it was impossible to determine which antibody was derived from a human or monkey without analysis of the source itself.

Thus, for example, referring to FIG. 10, the amino acid sequence of the VH3 region of human was compared with monkey. The human antibodies showed a range of homology among themselves from 83–98%, while those of the monkey were from 90–95% homologous with the human VH3 region. In contrast, the human VH2 region was homologous to the human VH3 by 60%. [In this drawing, as in the other drawings, the presence of the same amino acid at any location is shown by a dash, while the presence of a different amino acid is shown by the standard one letter code. Positions to which no consensus amino acid can be assigned are shown as an X.] Similarly, homology for VH1, VH2, VH3, VH4, and VH5, and for VKI and VKII and Vlambda III is shown in FIGS. 9A–9H, respectively. Again, significant homology between the monkey immunoglobulin region and that of the human was observed in each variable region including immunoglobulin J regions sequences. Such high homology is similar to that observed among human antibodies.

The methodology by which the sequences were determined is presented below in the examples. Those of ordinary skill in the art will recognize that these examples are not limiting in this invention and equivalent results and monoclonal and chimeric antibodies can be obtained by similar procedures well known to those of ordinary skill in the art. See e.g., U.S. Pat. Nos. 4,816,567; 4,978,745; 4,975,369; 4,816,397, supra. For example, after cloning a gene encoding a monkey variable region, such a gene is readily ligated to one encoding a monkey or human constant region, and the fused genes expressed in a producer cell line to produce the desired antibody. Below are provided examples of such procedures.

In the following examples, the first step in the method involves the isolation of total RNA from monkey peripheral blood or spleen cells. B cells from immunized monkeys may be obtained from peripheral blood or lymph nodes and used directly or, they may be preferentially expanded. Expansion may involve *Herpes papio* virus transformation, fusion to a heterologous myeloma cell with subsequent selection, or cloning of single B cells under limiting dilution in the presence of stimulated human T cells.

Total RNA is then converted to single stranded (ss) cDNA by reverse transcriptase using non-specific (oligo-dT or random hexamers) or specific (immunoglobulin CH1 or CK or Clambda constant region) oligonucleotide primers. Single-stranded cDNA produced by this reaction is amplified using the polymerase chain reaction in which ss cDNA, together with deoxynucleotide triphosphates, a DNA polymerase. (e.g., a thermostable polymerase) and specific primers, are used to amplify heavy or light chain variable region immunoglobulin genes. The primers used are single stranded synthetic oligonucleotides ranging from 20 to 40 bases, containing some degenerate bases which bind to the immunoglobulin 5' leader sequences. Six different 5' leader sequence primers (see, FIG. 7-1 incorporating a restriction enzyme site (e.g., SalI) have been designed for amplification of monkey heavy chain variable region families based on their similarity to human heavy chain variable region gene families. With each of the six 5' leader sequence primers, a 3' primer specific for the constant region domain of the relevant isotype (e.g., IgG, IgM, IgA or IgE) also incorporating a restriction enzyme site (e.g., NheI) is used. Similarly, for monkey kappa and lambda light chains, other pairs of primers are used for amplification of the appropriate light chain variable region (FIG. 7-2).

Other sets of primers can be used in order to incorporate different, unique restriction sites to allow directional cloning of PCR-amplified DNA into an appropriate expression vector possessing the same restriction site. A set of primers binding to the 3' end of the antibody heavy chain leader sequence incorporating a Mlu1 site, or a set of primers binding to the first 23 bases of framework one incorporating a XhoI site can also be used and are described in FIG. 7-1. The monkey immunoglobulin heavy and light chain variable region genes may be cloned into a shuttle vector directly after PCR amplification to allow further molecular manipulations if necessary or, cloned directly into an expression vector that contains human heavy or light chain constant region genes. The molecular configuration of the immunoglobulin genes in the expression vector may be genomic, in which immunoglobulin promoter/enhancer and other regulatory regions are present as well as splice donor/acceptor sequences at the intron/exon junctions. Alternatively, chimeric immunoglobulin genes can be inserted in a cDNA configuration using heterologous viral promoter/enhancer sequences.

EXAMPLE 1

Sequence of Monkey Antibodies

FIGS. 7 and 8 show the primers with or without restriction sites respectively, used in the PCR amplification of immunoglobulin genes from monkey and/or human cDNAs. Details of the procedures used are provided below. RNA was isolated from the spleen, peripheral blood and lymph node cells of monkeys using the standard guanidinium isothiocyanate method. The total RNA fraction isolated by this method was then used as a template for subsequent amplification reactions. An aliquot of the RNA was incubated in the presence of 200 units of Moloney murine leukemia virus reverse transcriptase and non-specific (oligo-dT or random hexamers) or specific (immunoglobulin IgG CH1 region or kappa chain constant region CK) oligonucleotide primers (50–100 picomoles) to generate a non-coding sense single cDNA strand. Single stranded cDNA produced by this reaction was then amplified using the polymerase chain reaction (PCR). An aliquot of single stranded cDNA was incubated together with deoxynucleotide tri-phosphates (20 µM), a thermostable DNA polymerase (2–5 units) and human-derived synthetic oligonucleotide primers (50 picomoles), to amplify either heavy or light chain variable region immunoglobulin genes.

Using pairs of primers shown in FIG. 8, several representative cynomolgus immunoglobulin heavy and light chain variable region sequences from a number of gene families were amplified. These amplified sequences were cloned into the EcoRV site of the plasmid vector p-Bluescript (pBS, available from Stratagene, Calif.) and used for DNA sequencing. DNA sequencing was performed using the plasmid DNA containing the cloned insert as a double stranded DNA template and the standard chain termination sequencing method.

Representative cynomolgus monkey immunoglobulin sequences are shown in FIGS. 9A–9H. Included in FIGS. 9A–9H are the consensus amino acid sequence for human variable region genes representing each of the major variable region gene families. The percentage homology of each monkey sequence with the human consensus sequence, excluding the constant domain regions and the CDR regions, is shown. The level of homology between human and monkey sequences for a given family is as high as between two human sequences within that family. It is impossible therefore to distinguish between variable region immunoglobulin sequences originating from Old World monkeys, and those originating from humans based on sequence comparisons alone.

Isolation of RNA

Monkey antigen-specific B cells were obtained in several ways: by fusion of immunized monkey lymph node cells to the human/mouse heteromyeloma fusion partner cell line K5H6/B5, and subsequent screening of the hybridoma lines, by virally transformed B cells, or by in vitro single B cell cloning techniques. In the latter case growth of a single monkey B cell was supported in vitro by co-cultivation with human T cells that were stimulated by antibody. A single B cell was placed in each well of a 96 well tissue culture plate together with approximately 150,000 anti-CD3-stimulated mytomycin C-treated human T cells. After a two week incubation period the single B cell expanded to at least 200 differentiated plasma cells. Culture supernatant from these wells were assayed for the presence of immunoglobulin by ELISA technique using a capture antibody of goat anti-monkey immunoglobulin.

Cells either from antigen-specific virally transformed cells or hybridomas were grown up in sufficient numbers for extraction of RNA. Wells from the in vitro single B cell cloning technique that were positive for immunoglobulin were removed, washed twice with cold phosphate buffered saline pH 7.5 and centrifuged (1000× g 10 min). The washed cells were suspended in 100 µl of lysis solution (4M guanidinium isothiocyanate, 25 mM sodium citrate pH 7.0, 0.5% sodium sarcosine, 0.1M 2-mercaptoethanol). 10 µl of 2M sodium acetate, pH 4.0, was added and mixed. Protein was removed by adding 100 µl water saturated phenol, mixing and adding 20 µl of chloroform/isoamyl alcohol (49:1). After vortexing and incubation on ice for 15 min, the samples were centrifuged at 10,000× g for 20 minutes. The aqueous phase was transferred to a new tube, mixed with an equal volume of isopropanol and incubated for 1 hr at −20° C. The precipitate was collected by centrifugation at 10,000× g for 15 minutes, washed with 70% ethanol, recentrifuged and the pellet dried in a Speedivac (Savant). The dried RNA was redissolved a second time in 100 µl of lysis buffer. An equal volume is isopropanol was added and incubated at −20° C. for one hour. The precipitate was collected by centrifugation at 10,000× g for 15 minutes and washed with 70% ethanol. The pellet was dried in a Speedivac (Savant) and stored at −20° C. in 70% ethanol until use.

Synthesis of single stranded cDNA

The total RNA extracted from the cells originating from a single well was dissolved in 32 µl of double distilled water to which is added 1 µl (50–100 picomoles) of primer (either random hexamers, oligo dT or 3' immunoglobulin-specific primers) and 10 µl of 5× reverse transcriptase buffer (0.25 Tris-HCl pH 8.3, 0.375M KCl, 15 mM MgCl$_2$, 50 mM dithiothreitol). The mixture was heated at 65° C. for 5 minutes after which it was placed in ice for 2 minutes. After heating, 1 µl RNAsin (Promega), 5 µl of 5 mM deoxynucleotide triphosphates, and 1 µl (200 units) of Moloney murine leukemia virus reverse transcriptase (BRL) was added, and the mixture incubated at 37° C. for 1.5 hours. After completion of the reverse transcriptase reaction, the single stranded cDNA/RNA mixture was extracted with phenol/chloroform and passed through a 1 ml G-25 SEPHADEX spin column. The material passing through this column was used as template ss cDNA for PCR amplification.

Amplification of ss cDNA

3–10 µl of the ss cDNA was mixed with 10 µl 10× PCR buffer (500 mM KCl, 100 mM Tris-HCl pH 8.3, 15 mM MgCl$_2$), 1.6 µl of 1.25 mM deoxynucleotide triphosphates, 50 picomoles of specific immunoglobulin 5' primer, 50 picomoles of specific immunoglobulin 3' primer, and 2–5 units of thermostable DNA polymerase (Synthetic Genetics). The reaction volume was brought to 100 µl with water and overlaid with 100 µl of mineral oil. The reaction mixture was incubated at the following temperatures for the specified times:

94° C. for 1 minute
48° C. for 2 minutes
72° C. for 2 minutes

This cycle was repeated 30–35 times. The amplified products were examined by agarose gel electrophoresis using a 1.2% agarose gel and molecular weight standards. The amplified immunoglobulin variable region genes ran approximately between 350–500 bp markers. The PCR amplified products were then used for cloning into the appropriate plasmid vector.

EXAMPLE 2

Cloning Monkey Antibody Genes

Because monkey variable region gene sequences, at the cDNA level, are indistinguishable from human members of the equivalent gene family, immune responses to monkey/human chimeric antibodies, if any, are unlikely to be any different than those mounted against human antibody molecules.

Figure 6:
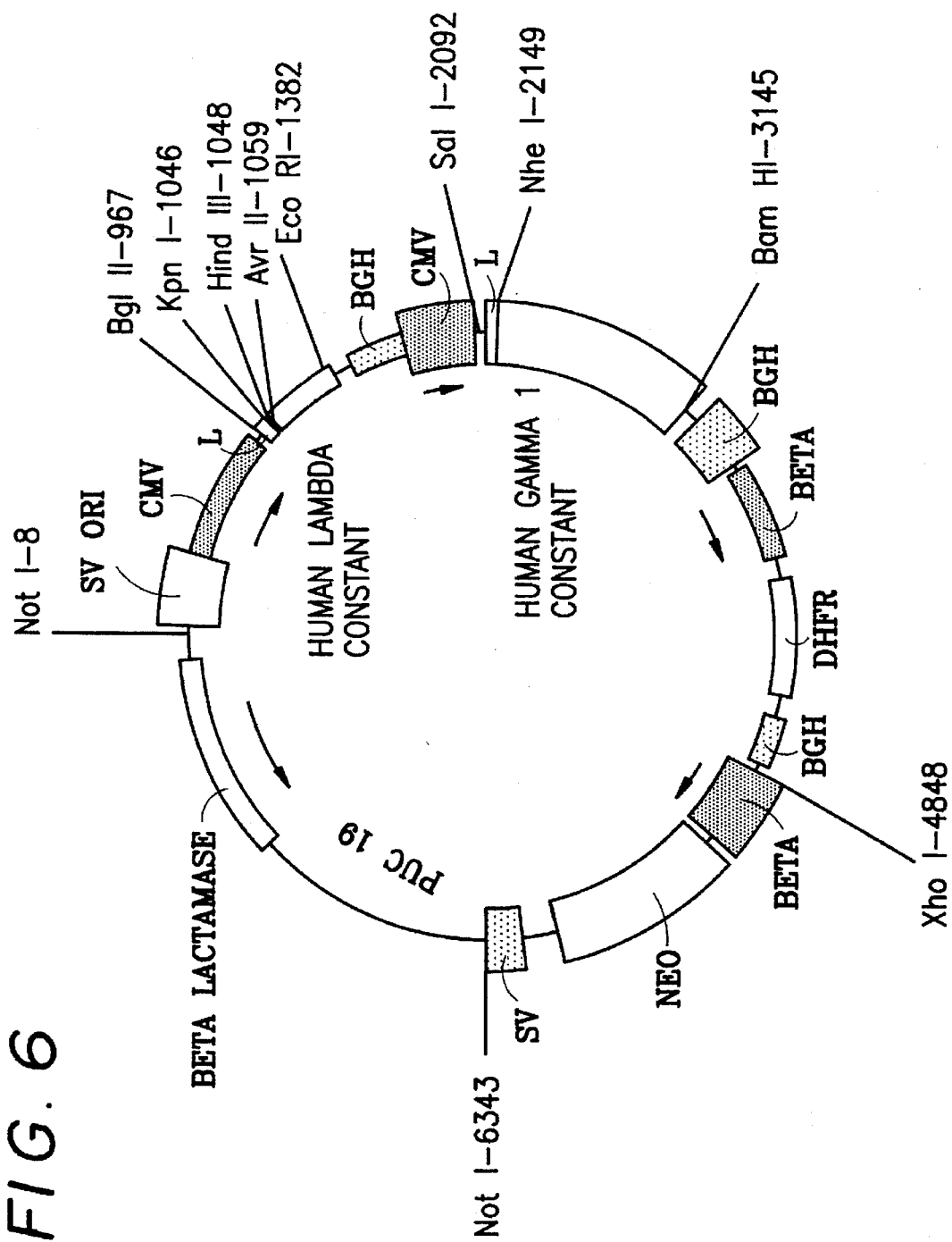

PCR technology can be used to introduce specific restriction enzyme sites, including (but not limited to) SalI, BglII, KpnI and NheI, into the Old World variable region sequences during the PCR amplification reaction using primers based on those in FIG. 6. Pre-existing cloned genes were amplified from their specific vector using these primers to introduce the specific restriction site which was subsequently used to clone the gene into an expression vector. Alternatively, these primers were used to amplify directly from cellular RNA.

Expression vectors which have been constructed are of two types. The first (see FIGS. 3 and 4) allows cloned cDNA immunoglobulin variable regions from monkeys to be inserted into a cassette vector, using unique restriction sites, in which the immunoglobulin gene elements are arranged in a genomic configuration. This type of vector incorporates an immunoglobulin promoter, the two exons making up the immunoglobulin leader sequence, two cloning sites SpeI and NheI, downstream splice donor sequences, an immunoglobulin enhancer region, a human constant region gene (heavy or light chain) and downstream polyadenylation signals. In addition, they include a bacterial origin of replication, a beta-lactamase gene for bacterial selection, and a neomycin phosphotransferase gene for G418 selection, or a xanthine-quanine phosphoribosyl transferase (gpt) gene for mycophenolic acid selection in mammalian cells. The heavy and light chain expression vectors use neomycin phosphotransferase (Neo) and xanthine-guanine phosphoribosyl transferase (Gpt) genes respectively as the selectable marker.

The second type of expression system (see FIGS. 5 and 6) uses immunoglobulin genes in a cDNA configuration. That is, no introns or splice sites are present between the 5' leader sequence and the 3' constant region sequences. This type of vector utilizes heterologous viral promoter/enhancer sequences, driving immunoglobulin heavy and light chain genes arranged in a tandem fashion, polyadenylation sequences and a selectable mammalian cell marker (Neo). The Neogene can be modified to weaken its translation, e.g., by changing the codon upstream and adjacent the start site of the gene from ACC to TCT. In addition, a dihydrofolate reductase (dhfr) gene is present for subsequent gene amplification with methotrexate. Monkey immunoglobulin variable region genes to be cloned into cDNA configured expression vectors were amplified either from pre-existing cloned sequences in the shuttle vector (PBS), or directly from RNA with primers containing either the restriction sites SalI or MluI and NheI, for heavy chain, or BglII and KpnI or BsiWI for kappa or lambda light chains. Other potential unique restriction sites however are not excluded.

Chimeric heavy and light chain immunoglobulin genes were introduced separately or sequentially (for genomically configured constructs), or on the same vector (for cDNA configured constructs), by electroporation into a producer cell line. Electroporation was used to introduce linearized DNA constructs into either Chinese hamster ovary (CHO) cells, or mouse myeloma cells, followed by single cell cloning of the transfectants into 96 well tissue culture plates. Electroporation conditions using a BTX-100 (BTX, San Diego) electroporation device and a 1 ml disposable plastic cuvette gave optimal numbers of transfectants from a given amount of vector DNA. CHO cells that were adapted to grow in suspension in serum-free medium (CHO-S SFM II minus hypoxanthine and thymidine, Gibco) were used in constructs containing viral regulatory elements.

Subcloning Ig variable region genes

The products of the PCR reaction were extracted with phenol/chloroform and passed through a 1 ml SEPHADEX G-25 spin column. If the DNA fragment was to be blunt end cloned into a plasmid 1 µl 1M MgCl$_2$, 0.5 ml of 1.25 mM deoxynucleotide triphosphates and 1 µl of Klenow DNA polymerase (5 units) was added to the total PCR reaction mixture (100 µl) and incubated at 37° C. for 15 minutes to fill in any 5' overhangs. Before blunt end cloning into a plasmid, the 5' ends were phosphorylated as follows; 5 µl of 10 mM ATP, 1 µl of T4 polynucleotide kinase (10 units) were added to the total reaction mix and incubated at 37° C. for 30 minutes. Amplified fragments that contained internal restriction sites were first cut with the appropriate restriction enzyme and used directly for ligation without phosphorylation. In both cases the fragment to be cloned was extracted with phenol/chloroform before ligating into the appropriate vector.

For the ligation reaction 10% of the phosphorylated or restriction enzyme cut-PCR amplified fragment was mixed with approximately 2 ng of appropriate vector (total volume 8 µl), previously digested with the restriction enzyme(s). For blunt end-cloning pBluescript digested with EcoRV was used. For sticky end cloning the vector TCAE 5.2 or 6.0 or pGenex-H or pGenexL, cut with appropriate restriction enzymes was used. 1 µl of 10× ligation buffer (500 mM Tri-HCl pH 7.6, 100 mM MgCl$_2$, 10 mM ATP, 10 mM dithiothreitol), 1 µl T4 DNA ligase (1 unit) was added and the reaction allowed to proceed at 14° C. overnight. The ligated material was used to transform competent E. coli HB101 cells using the standard calcium chloride method of transformation. The transformed bacteria were selected by growth on LB ampicillin-containing agar plates. Individual colonies were selected and grown up overnight in LB medium containing ampicillin and plasmid DNA extracted using the standard alkaline lysis method. After restriction analysis to determine which clones contained immunoglobulin inserts, the DNA was prepared for sequencing.

Sequencing cloned genes

Cloned immunoglobulin variable region genes were sequenced using a standard chain termination method. Double stranded plasmid DNA containing the cloned insert was used as the sequencing template. Before sequencing, the double stranded DNA was chemically denatured. DNA was sequenced using T7 DNA polymerase SEQUENASE (United States Biochemical Corporation, Cleveland, Ohio), radiolabeled alpha deoxyATP, and the following sequencing primers: (5' CAGAGCTGGGTACGTCCTCA 3') and (5' GCCCCCAGAGGTGCTCTTGG 3') for immunoglobulin G heavy chain variable region in 5' to 3' and 3' to 5' directions respectively. (5' CAGAGCTGGGTACGTGAACC 3') and (5' GGCTTGAAGCTCCTCAGAGG 3') for immunoglobulin lambda light chain variable region in 5' to 3' and 3' to 5' directions, respectively. Reaction products were separated on 6% polyacrylamide gels and read.

The results of sequencing a number of Old World monkey immunoglobulin heavy and light variable region genes are summarized in FIGS. 9A–9H. Cloning and sequencing cynomolgus immunoglobulin genes has not been previously described in the literature. Nor, therefore, has the degree of homology between human and cynomolgus V region genes been possible to define. The homology between a single chimpanzee variable lambda gene and its human genomic counterpart has been described showing only a 2% difference in the framework regions.

Transfection and selection

Figure 3:
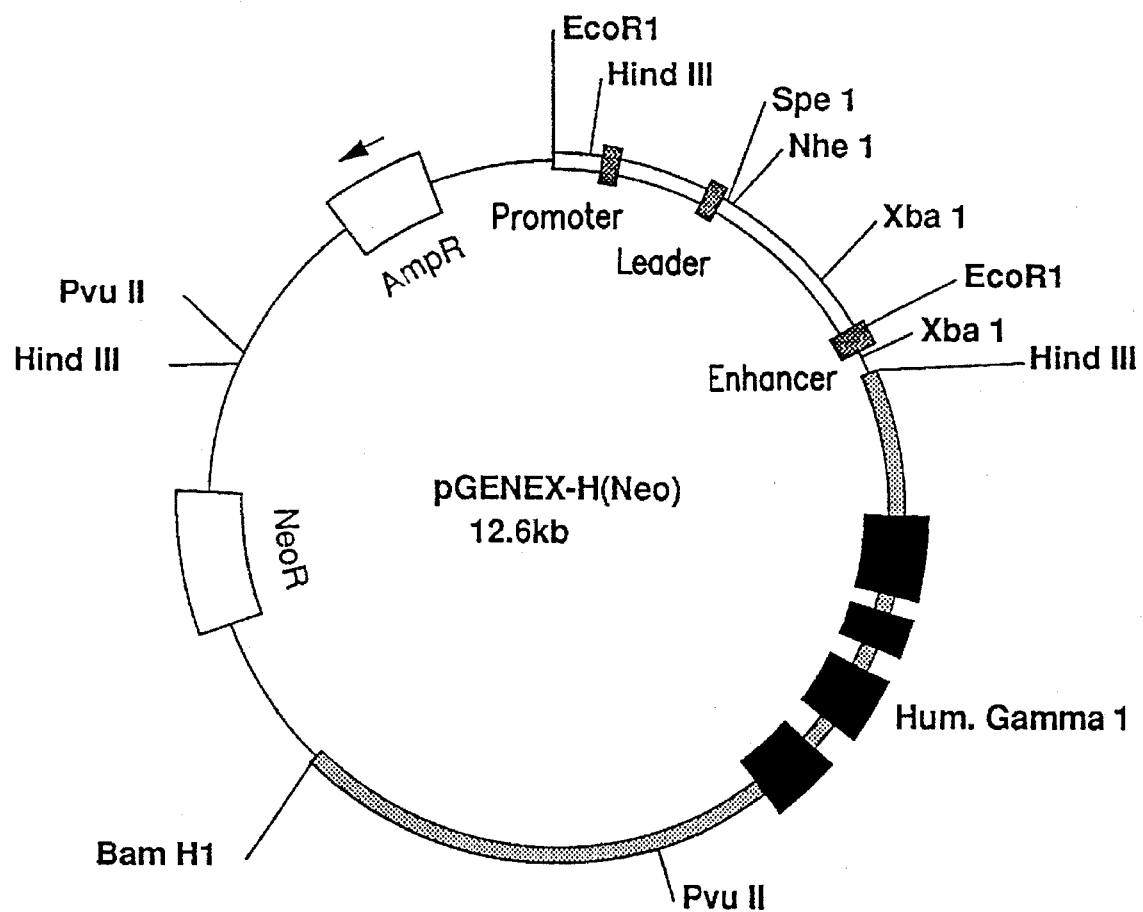
FIG. 3 is a diagrammatic representation of a heavy chain cassette vector for expression of human or chimeric antibodies.
Figure 4:
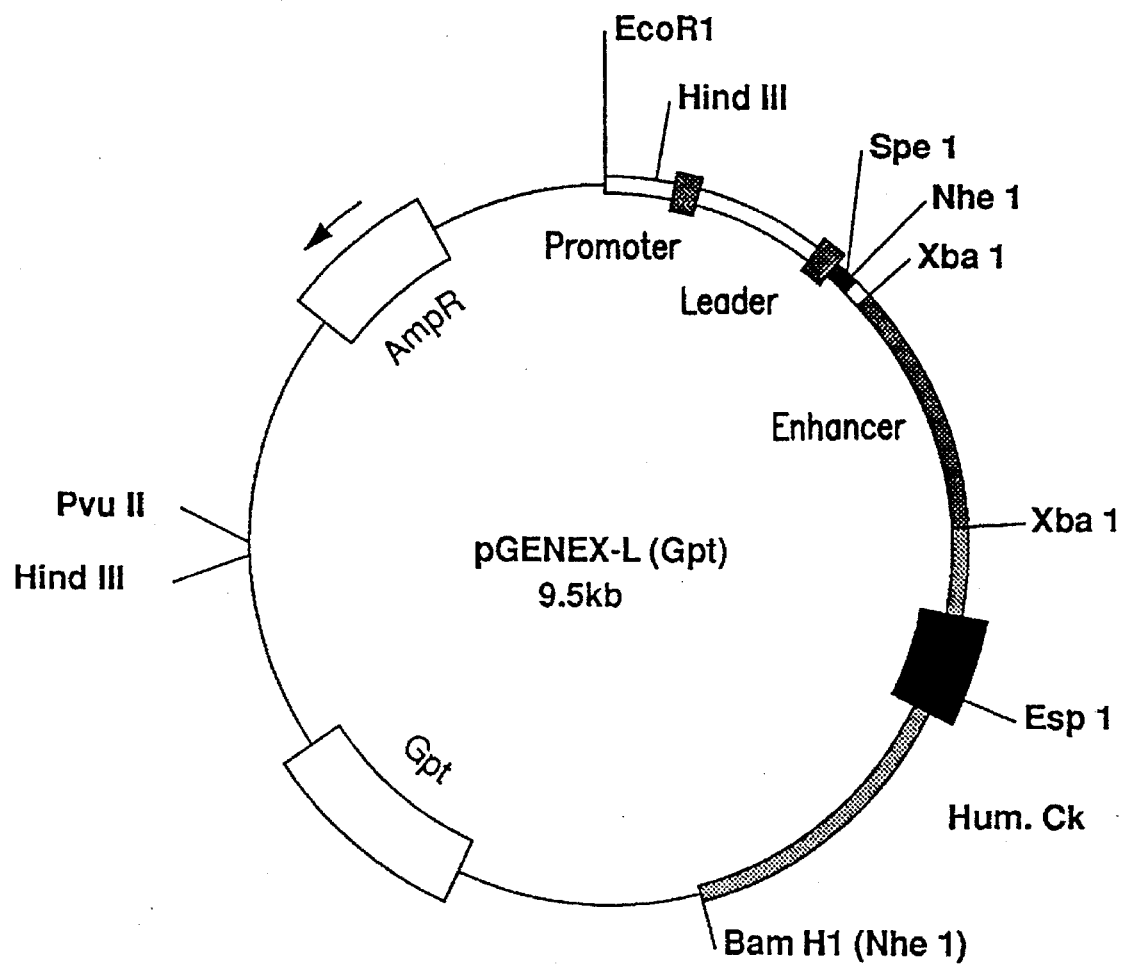
FIG. 4 is a diagrammatic representation of a light chain cassette vector designed for expression of human or chimeric antibodies.
Figure 5:
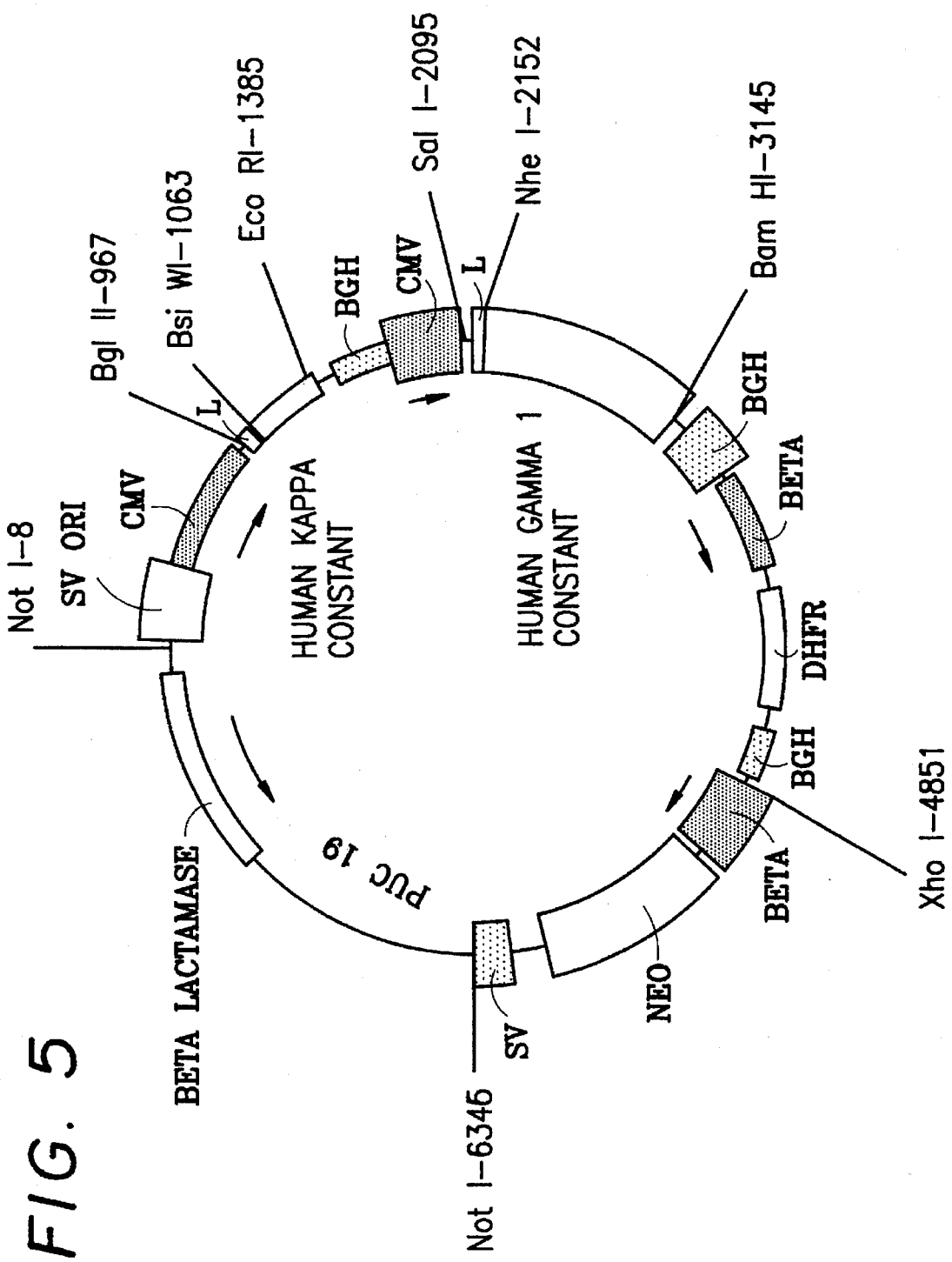
FIGS. 5 and 6 are diagrammatic representations of vectors designed for expression of immunoglobulin from kappa or lambda light chain cDNA, respectively. In these vectors, the immunoglobulin genes are arranged in a tandem configuration using neomycin phosphotransferase as the selectable marker.

After sequencing cloned heavy and light chain variable region genes, they were sub-cloned into appropriate vectors for expression. These may be vectors constructed with immunoglobulin regulatory elements in a genomic configuration (as shown in FIGS. 3 and 4), or with viral regulatory elements using a cDNA configuration (FIGS. 5 and 6). Appropriate restriction sites (SpeI and NheI) can be designed into the PCR amplification primers during the initial amplification step, or conversely amplification primers containing restriction sites can be used to amplify immunoglobulin genes from the shuttle vectors into which they have been cloned. Alternatively, immunoglobulin variable region genes may be cloned directly into expression vectors after PCR amplification from RNA, so that subcloning is unnecessary.

Electroporation

Electroporation was used to either co-transfect heavy and light chain genomic constructs or sequentially transfect heavy and light chain genomic constructs into Sp2/0 cells. In sequential transfections electroporation of the chimeric light chain construct was followed by selection in mycophenolic acid. Screening culture supernatants from clones, grown in 96 well plates, for light chain production with antisera against human light chain constant region using an ELISA technique, allowed selection of the highest light chain expressing clones. Subsequent electroporation of light chain transfectants with a vector containing the monkey/human chimeric heavy chain immunoglobulin construct allowed the selection of transfectomas expressing chimeric antibody of the desired specificity and isotype.

The light chain construct pGENEX-L (FIGS. 3 and 4) was transfected into the murine myeloma cell line Sp2/0 by electropotation as follows. SP2/0 cells at a concentration of $1 \times 10^7$/ml in transfection buffer (272 mM sucrose, 7 mM sodium phosphate pH 7.4, 1 mM $MgCl_2$) were mixed with 50 ug of pGENEX-L containing the appropriate cloned light chain gene, which had previously been linearized by digestion with the restriction enzyme PvuII. The cells were placed into a 1 ml disposable plastic spectrophotometry cuvette and plate electrodes 3.5 mm apart inserted into the cuvette. Using a BTX-100 (BTX, Inc.) transfection apparatus the cells were given a pulse of current for 500 microseconds such that approximately 50% cell death occurred. This value was determined prior to the transfection by pulsing the cells, in the absence of DNA, with increasing voltages and measuring the numbers of cells surviving 24 hours later. The voltage versus cell viability was plotted graphically and the voltage corresponding to 50% cell death used for all subsequent electroporation experiments. Using the BTX-100 apparatus, the optimal value was found to be a pulse at an amplitude of 200 for 500 microseconds. After pulsing the cells, they were allowed to recover on ice for 15 minutes before being transferred to 96-well tissue culture plates in Dulbecco's modified Eagle's medium (DMEM) containing 5% fetal calf serum and 10% Sp2/0 conditioned medium. Cells were plated at a concentration at which cell growth was seen in approximately 1 in 3 of the wells after selection with the appropriate drug. This parameter was determined for each electroporation experiment by plating varying numbers of electroporated cells per well (1000–10,000) and selecting for cells which have incorporated the plasmid. The number of wells on each plate which showed cell growth was counted after 2–3 weeks of selection. Thus, the appropriate number of cells that gave 1 out of 3 positive wells with a given concentration of a particular plasmid was determined for use in future experiments.

Directly after electroporation cells were placed in medium without drug. Fresh medium was added two days after electroporation containing either G418 or mycophenolic acid for cells exhibiting neomycin phosphotransferase or guanasyl phosphotransferase activity respectively. Cells were fed every 2 days for the first week and then twice a week thereafter. The concentration of drug to use was determined by incubating cells in the presence of increasing concentrations of drug and monitoring cell viability. The concentration of drug used was twice that which gave 100% killing. For Sp2/0 approximately 1 µg mycophenolic acid/ml was required and for G418 approximately 800 µg/ml.

Cells were electroporated in several ways, either heavy and light chain genomic vectors (pGenex-H and pGenex-L) were co-electroporated, or the light chain was electroporated alone. In the latter case, clones were screened for high level expression of chimeric immunoglobulin light chain using an ELISA technique. These clones were then grown up and electroporated with heavy chain containing vector. If cDNA tandem gene constructs were used, the expression vector (TCAE5.2 or TCAE6) was first linearized by digestion with the restriction enzyme NotI. A single electroporation was sufficient to achieve integration of both heavy and light chain genes. After 2–3 weeks supernatants from wells which continue to grow in the presence of appropriate drug were assayed for the secretion of chimeric immunoglobulin light chain or whole immunoglobulin using an ELISA technique. Immunoglobulin genes in a cDNA configuration were electroporated into either Sp2/0 cells, as described above, or into Chinese Hamster Ovary (CHO) cells adapted to grow in suspension in serum-free medium. CHO cells were electroporated using a BTX 600 electroporation apparatus, set at conditions for achieving maximal numbers of G418 resistant colonies. These were 210 volts, 400 µF and 13 ohms. After electroporation, cells were counted, washed in transfection buffer, resuspended in the same buffer and placed on ice for 15 minutes. Cells were adjusted to $1 \times 10^7$ live cells/ml and 400 µl of cell suspension placed in a 0.4 ml sterile disposable cuvette (BTX Inc.). 25 µg of Not 1 linearized TCAE 5.2 or TCAE 6 vector DNA, containing cloned macaque immunoglobulin variable region genes, were resuspended in TE buffer (10 mM Tris, 1 mM EDTA, pH 8.0) at 1 µg/ml and added to the cell suspension. Electropotation was carried out by discharging the apparatus using the automatic charge and pulse button. The cuvette was placed on ice for 15 minutes, the cells diluted into 120 mls of serum-free medium and placed into six 96-well plates (200 µl per well containing approximately 6,667 electroporated or 3,333 live cells per well). Independent electroporation parameters were established for this cell line and selection by G418 was at 400 µg/ml.

Screening for production of antibody

The presence of human, monkey or chimeric antibody secreted by transfectants was assayed by an ELISA technique as follows: 96-well flat bottom plates (Dynatech) were coated with goat anti-human IgG or kappa at 200 ng/well in Coating Buffer (sodium carbonate 0.8 mg/ml, sodium bicarbonate 1.55 mg/ml, pH9.6) and incubated for at least 16 hr at 4° C. The coating buffer was removed and the wells blocked with 120 µl of Blocking Buffer (1% bovine serum albumin in phosphate buffered saline containing 0.2% sodium azide) and incubated at 37° C. for 1 hr. Up to 125 µl of cell culture supernatant was added to the wells containing blocking buffer and incubated 2 hrs at 37° C. The plates were then washed five times with PBS. 100 µl of horse radish peroxidase-labeled goat anti-human IgG (or kappa) diluted 1:1000–1:5000 in Dilution Buffer (1% bovine serum albumin, 0.05% TWEEN-20, 0.02% sodium azide in PBS) was added. Plates were incubated at 37° C. for 1 hr then washed five times with PBS. Chimeric antibody was detected with 100 µl of hydrogen peroxide and the substrate, 3,3',5,5'-tetramethylbenzidine (1:1 v/v) per well. The color reaction was terminated after 2 to 5 min. with 100 µl of 2M sulfuric acid per well.

Those of ordinary skill in the art can readily perform equivalent methodologies to those described above. Examples of such technology include immortalization of selected B-cells by hybridoma fusion, as described above, with the cell line K5H6/B5 described by Carroll et al., 164 *J. Experimental Medicine* 1566, 1986, or an equivalent cell line, such as SPAZ4 (available from Sandoz, see, Ehrlich et al., 34 *Clin. Chem.* 1681, 1988). Similar cell lines can be readily constructed by standard techniques using publically available methodology. Alternatively, immunoglobulin genes may be cloned from: (a) cells immortalized by viral transformation with *Herpes papio*, as described by Markova et al., 30 *Vopr Virusol* 549, 1985, or with an equivalent virus, (b) by single B-cell cloning to provide a transient immortalization, as described by Amaroso and Lipske 145 *J. Immunology* 3155, 1990, or (c) by use of a recombinant immunoglobulin bacteriophage libraries, as described by Huse et al., 246 *Science* 1275, 1989 and McCafferty et al., 348 *Nature* 552, 1990. Screening for appropriate antibody containing clones can be performed by those techniques described above, or equivalent techniques well known to those of ordinary skill in the art, and the desired immunoglobulin gene rescued from the immortalized cell line. In addition, the antibody produced by isolated monkey B cells can be used in human therapy, without manipulation to form a chimeric antibody.

The human constant region may be obtained by standard techniques, with any desired isotype well known to those of ordinary skill in the art, and the variable region of a monkey antibody ligated with that human constant region. Particularly useful chimeric antibodies against specific cell surface receptors which can be used in immunotherapy of humans include CD4, ICAMs, CD19, CD20, CD8, CD11a, CD11b, CD28, CD18, CD45, CD71, and TCR.

EXAMPLE 3

Cloning and Expressing a Monkey/Human Chimeric Antibody with Specificity for CD4

The following is a specific example of the methods and antibodies of this invention.

Generation of Monkey Immortalized B-cell Lines

An adult cynomolgus monkey (White Sands New Mexico Primate Center) was immunized intramuscularly, at multiple sites, with 150–300 µg of soluble CD4 (sCD4) or cell membranes ($1\times10^8$ cells) from the CD4 positive cell line supT1 using a standard adjuvant. Immunization was repeated every 2–3 weeks for a total of six times. The monkey was boosted by injection of 100 µg of sCD4 into the inguinal region of one thigh and one week later the draining lymph node from the same thigh surgically removed. Lymphocytes were removed from the lymph node by slicing the tissue and rinsing with sterile DMEM medium. The cell suspension was passed through a nylon gauze and collected by centrifugation at 1000× g for 10 minutes.

Approximately $1\times10^8$ lymphocytes were suspended in Tris-ammonium chloride buffer (16 mM, pH 7.5) and warmed to 37° C. for 5 minutes to lyse the erythrocytes. Lymphocytes were collected by centrifugation and resuspended in L-leucine methyl ester (LME) and incubated at 37° C. for 45 minutes. The LME treated cells were filtered through a nylon screen and centrifuged. 1 ml of fetal calf serum was added, the cells suspended and washed twice in serum-free RPMI. The cells were counted and mixed into a single 50 ml conical centrifuge tube together with an equal number of K6H6/B5 heteromyeloma cells, prewashed twice in serum free medium. Cells were gently suspended in 1 ml of 50% PEG (polyethylene glycol) added slowly with gentle stirring over a 1 minute period. The cells were then resuspended by the addition of 20ml of serum-free medium over a 5 minute period, with gentle mixing to dilute out the PEG. After washing twice with serum-free medium cells were resuspended at a concentration of $5\times10^5/0.1$ ml in RPMI medium, containing 20% fetal calf serum and gentamycin and placed into 96 well micro tissue culture plates at 0.1 ml per well. An equal volume of HAT medium (0.1 ml) was added to each well and the hybrids allowed to grow for 14–17 days before screening.

Screening of Fused Cell Hybrids for the Production of Anti-CD4

The assay to determine anti-CD4 specificity was as follows: ELISA plates were coated with recombinant sCD4 at a concentration of 100 ng per well and blocked with 1% bovine serum albumin in PBS. 50 µl aliquots of hybridoma supernatant were removed from each well and allowed to incubate with the sCD4 coated plates for 60 minutes. Binding was detected by incubation with $^{125}$I labeled goat anti-human or goat anti-monkey Ig for 60 minutes. After washing four times with distilled water, the wells were counted in a gamma counter. Positive wells were re-assayed in duplicate and the hybridoma cells from those wells subcloned three times, first at 5 cells per well then twice at 1 cell per well. At this stage anti-sCD4 positives were screened for the ability to bind to cell surface CD4. This was done by inhibition of binding of an anti-CD4 murine monoclonal, termed 1F3, to the CD4 positive cell line supT1. Briefly this was done by co-incubating different amounts of monkey anti-CD4 and 10 ng of $^{125}$I-labeled 1F3 with $3\times10^5$ supT1 cells/well in a 96 well plate. After incubation for 1 hour at room temperature (about 20°–25° C.) cells were removed by vacuum onto glass fiber filters. After extensive washing with PBS the filters were counted in a gamma counter to determine the inhibition of 1F3 binding to supT1 cells by the monkey hybridoma supernatants.

A candidate clone was chosen which produced an antibody that showed strong inhibition against 1F3. The clone we chose was isotyped using human isotyping reagents and found to be an IgG2 possessing a lambda light chain. This cell line was grown up to larger numbers for cloning of its immunoglobulin genes.

Cloning of Heavy and Light Chain Variable Region Genes from Monkey Immortalized B-cells Total RNA was isolated from $1\times10^7$ monkey immortalized B-cells using the guanidinium isothiocyanate method described above. One tenth of the total RNA was used to make single stranded cDNA using an oligo-dT oligonucleotide primer and reverse transcriptase, also as described above. One tenth of the amount of ss cDNA was used to set up PCR reactions. The six PCR reactions each included one of six 5' $V_H$ family specific oligonucleotide primers containing a Sal I restriction site together with an IgG 3' constant region oligonucleotide containing an Nhe I site, both shown in FIG. 7-1. Similarly, five PCR reactions, utilizing one of five 5' lambda leader sequence oligonucleotide primers containing a Bgl II site and a 3' lambda constant region prime containing an Avr II site, were run. Reaction conditions were as described above. Each PCR reaction was run in triplicate. The products of each of the heavy chain and light chain amplification reactions were run on 1.2% agarose gels. The VH4 heavy chain primer (SEQ. ID. NO.: 13: 5' ACTAAGTCGACATGAAACACCTGTG-GTTCTT 3') and lambda primer (SEQ. ID. NO.: 14: (5' ATCACAGATCTCTCACCATGACCTGCT-CCCTCTCCTCC 3') gave strong bands on agarose gel electrophoresis. The products of these reactions were used for cloning into the vector TCAE 6, which contains human IgG1 and human lambda constant region sequences.

Cloning of the two variable region genes into the expression vector TCAE 6 was done sequentially. First, the heavy chain PCR product and the vector TCAE 6 were digested with the restriction enzymes Sal I and Nhe I, the products extracted with phenol/chloroform, and passed through a SEPHADEX G-25 spin column. The PCR product was ligated to the cut vector overnight at 14° C. in the presence of T4 DNA ligase. Approximately 500 ng total DNA was ligated in a volume of 10 µl with an insert/vector molar ratio of 10:1. Ligated material was used to transform XL-1 Blue competent cells (Stratagene) and the transformed cells plated onto LB agar plates containing 50 µg/ml ampicillin. Colonies of ampicillin resistant bacteria were picked and grown as 5 ml minicultures. Plasmid DNA was extracted from each of these cultures by a standard alkaline lysis method cut with the restriction enzymes Sal I and Nhe I and the products run on a 1.2% agarose gel. Plasmids with inserts of approximately 450 bp were used as templates for the subsequent cloning of light chain variable regions. The products of the light chain PCR reaction as well the plasmid containing the heavy chain insert were cut with the restriction enzymes Bgl II and Avr II and ligated together. Plasmid minicultures were screened by cutting with Bgl II and Avr II. Digests giving an insert of approximately 400–450 bp were scored positive. Plasmids containing both Sal I/Nhe I and Bgl II/Avr II inserts were grown up in larger quantities for DNA sequencing.

The tandem chimeric antibody expression vectors TCAE 5.2 and TCAE 6 were derived from the vector CLDN, which itself is a derivative of the vector RLDN10b (253 Science 77–79, 1991). RLDN10b in turn is a derivative of the expression vector TND (7 DNA 651–661, 1988)

RLDN10b differs from the vector TND in the following ways. The dihydrofolate reductase (DHFR) transcriptional cassette (promoter, cDNA, and polyadenylation region) was placed inbetween the tissue plasminogen activator cassette (t-PA expression cassette) and the neomycin phosphotransferase (NEO) cassette so that all three cassettes are in tandem and in the same transcriptional orientation. In addition, the DHFR gene promoter in CLDN has been replaced by the mouse beta globin major promoter (3 Mol. Cell Biol. 1246–54, 1983) and the t-PA cDNA replaced by a polylinker. All three eukaryotic transcriptional cassettes (Expression , DHFR, NEO) can be separated from the bacterial plasmid DNA (pUC9 derivative) by digestion with the restriction endonuclease NotI.

CLDN differs from RLDN10b because the Rous LTR in front of the polylinker has been replaced by the human cytomegalovirus immediate early gene promoter enhancer (41 Cell, 521, 1985).

The expression vectors TCAE 5.2 and TCAE 6 differ from CLDN in that:

1) They contain four transcriptional cassettes (instead of three), in tandem order:

(a) A human immunoglobulin light chain constant region derived via amplification of cDNA by a polymerase chain reaction. In TCAE 5.2 this is the human immunoglobulin light chain kappa constant region (Kabat numbering amino acids 108–214, allotype Km3), and in TCAE 6 the human immunoglobulin light chain lambda constant region (Kabat numbering amino acids 108–215, genotype Oz minus, Mcg minus, Ke minus allotype)

(b) A human immunoglobulin heavy chain constant region; in both constructs the human immunoglobulin heavy chain was a gamma 1 constant region (Kabat numbering amino acids 114–478 allotype Gm1a, Gm1z), which was derived via amplification of cDNA by a polymerase chain reaction.

(c) DHFR; containing its own eukaryotic promoter and polyadenylation region.

(d) NEO; also containing its own eukaryotic promoter and polyadenylation region.

3) The human immunoglobulin light and heavy chain cassettes contain synthetic signal sequences for secretion of the immunoglobulin chains 4) The human immunoglobulin light and heavy chain cassettes contain specific DNA linkers which allow for insertion of light and heavy immunoglobulin variable regions which maintain the translational reading frame and do not alter the amino acids normally found in immunoglobulin chains. The incorporation of the changes described, led to the construction of the vectors TCAE 5.2 and TCAE 6. The cloning of the immunoglobulin light and heavy variable region genes, from the anti-CD4 heterohybridoma cell line E9.1, into TCAE 6 led to the construct which is deposited in the ATCC. The construct, which has been deposited, contains the cynomolgus monkey immunoglobulin heavy chain variable region and cynomolgus monkey immunoglobulin light chain variable region, whose sequences are shown in FIGS. 13 and 14 respectively, cloned from the anti-CD4 hybridoma cell line E9.1. The heavy chain constant region is of human origin of the gamma 1 isotype and Gm1a, Gm1z allotype. The lambda light chain constant region is also of human origin, of the Oz minus, mcg minus genotype and Ke minus allotype. The immunoglobulin genes are cloned into the mammalian expression vector TCAE 6, shown in FIG. 6, which, when electroporated into the mammalian cell line CHO produced a monkey/human anti-CD4 chimeric antibody. The DNA construct described herein, has been used to transform the bacterial strain XL-1 Blue, selected in the antibiotic ampicillin and deposited as a bacterial cell suspension in sterile LB medium containing 15% glycerol.

Figure 16:
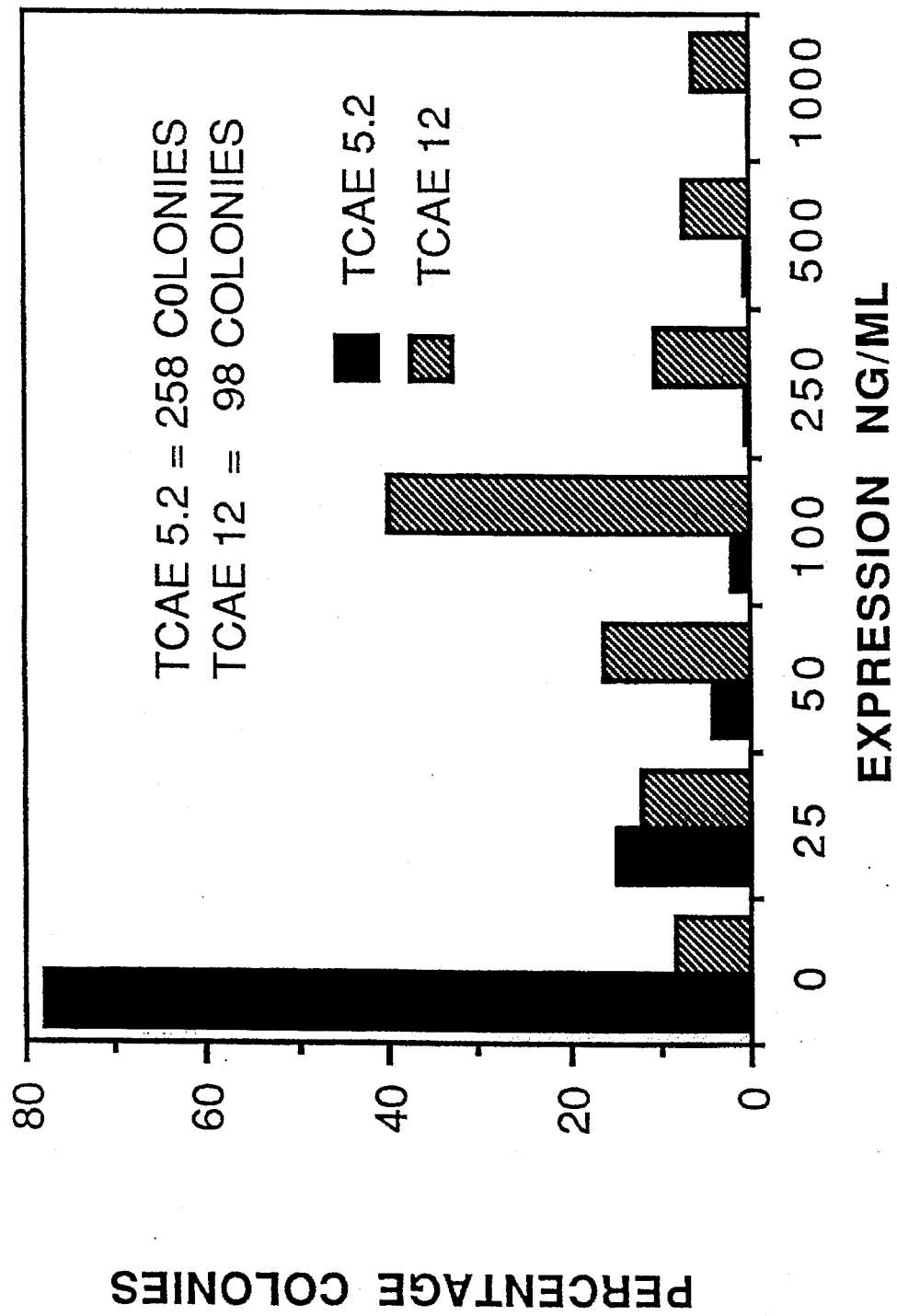
FIG. 16 is a histogram comparing plasmid expression features.

Another useful expression system is one in which the gene encoding a selective marker is modified to enhance yield of recombinant systems encoding a desired sequence. For example, translation initiation impairment of a dominant selectable marker results in fewer drug resistant colonies compared to a non-impaired vector, but each individual colony expresses significantly higher levels of colinked gene product than in the unimpaired vector. For example, translation initiation is the first step in protein synthesis. The translation initiation site of the neomycin phosphotransferase gene (G418 resistance gene) was changed from a consensus Kozak (sequence—ccAccATGG) to a poor Kozak (sequence—ccTccATGC). Translational initiation impairment of the G418 resistance gene resulted in: 1) a significant (5 fold) reduction in the number of G418 resistant colonies obtained from a same amount of plasmid DNA transfected per cell, and 2) a significant increase in the amount of colinked product gene expressed in each clone. In the clones containing the consensus Kozak 73% of the colonies screened produced less than 25 ng/ml, with only 3% producing greater than 100 ng/ml. For clones with the altered, poorer Kozak, 8% of the colonies screened produced less than 25 ng/ml, compared with 63% of colonies producing greater than 100 ng/ml. Specifically, referring to FIG. 16 (where TCAE 5.2 has a consensus Kozak, and TCAE 12 has a poorer Kozak), 258 colonies were derived from 2 electroporations of 25 µg of DNA which contains a neomycin phosphotransferase gene with a consensus (unchanged) translation start site. 201 of these colonies (78%) did not express any detectable gene product (i.e., <25 ng/ml of chimeric immunoglobulin), and only 8 colonies (3%) expressed more than 100 ng/ml. 98 colonies were derived from 6 electroporations of 25 µg of DNA which contains the neomycin phosphotransferase gene with an altered translation start site. 63% of these colonies were expressing more than 100 ng/ml, and only 8% of these colonies expressed less than 25 ng/ml.

DNA Sequencing

Plasmid DNA was prepared from 100 ml cultures. It was further purified by precipitating (1 volume) with a mixture of 2.5M sodium chloride and 20% polyethylene glycol (6 volumes) on ice for 15 minutes. After centrifugation at 10,000× g for 20 minutes, the pellet was washed with 70% ethanol, recentrifuged and dried in a Speedivac (Savant). The pellet of DNA was resuspended in deionized water at a concentration of 150–250 µg/ml. Sequencing was carried out on 5 µg of double stranded DNA using the technique of Sanger. Sequencing primers which were homologous to sequences within the expression vector upstream and downstream of either the light chain or heavy chain inserts were used. The inserts were sequenced in both. 5' to 3' and 3' to 5' directions. Two clones of anti-CD4 light chain and two clones of anti-CD4 heavy chain each generated from separate PCR reactions were sequenced in parallel in order to determine whether any nucleotide changes had been introduced during the PCR reaction. Both of the chosen heavy chain and both light chain clones were found to be identical over their entire length, confirming that no errors had been introduced during the amplification process. The sequence of the anti-CD4 heavy and light chains are shown in FIGS. 13 and 14 and Sequence Listing Nos.: 15 and 16.

Expression of Monkey/Human Chimeric Anti-CD4

Figure 11:
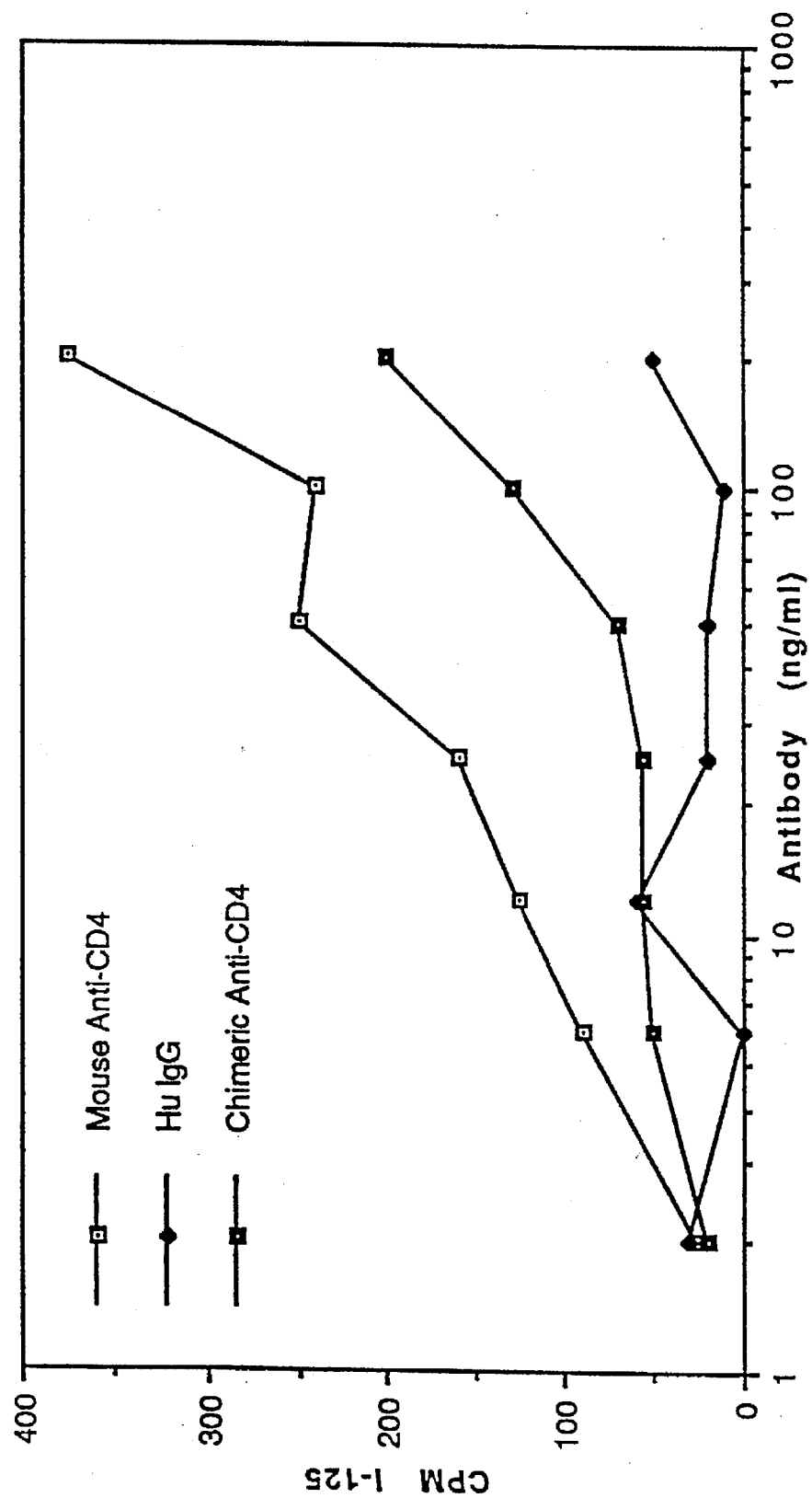
FIG. 11 is a graphical representation of the binding of an antibody of the invention to a human CD4 antigen.
Figure 12:
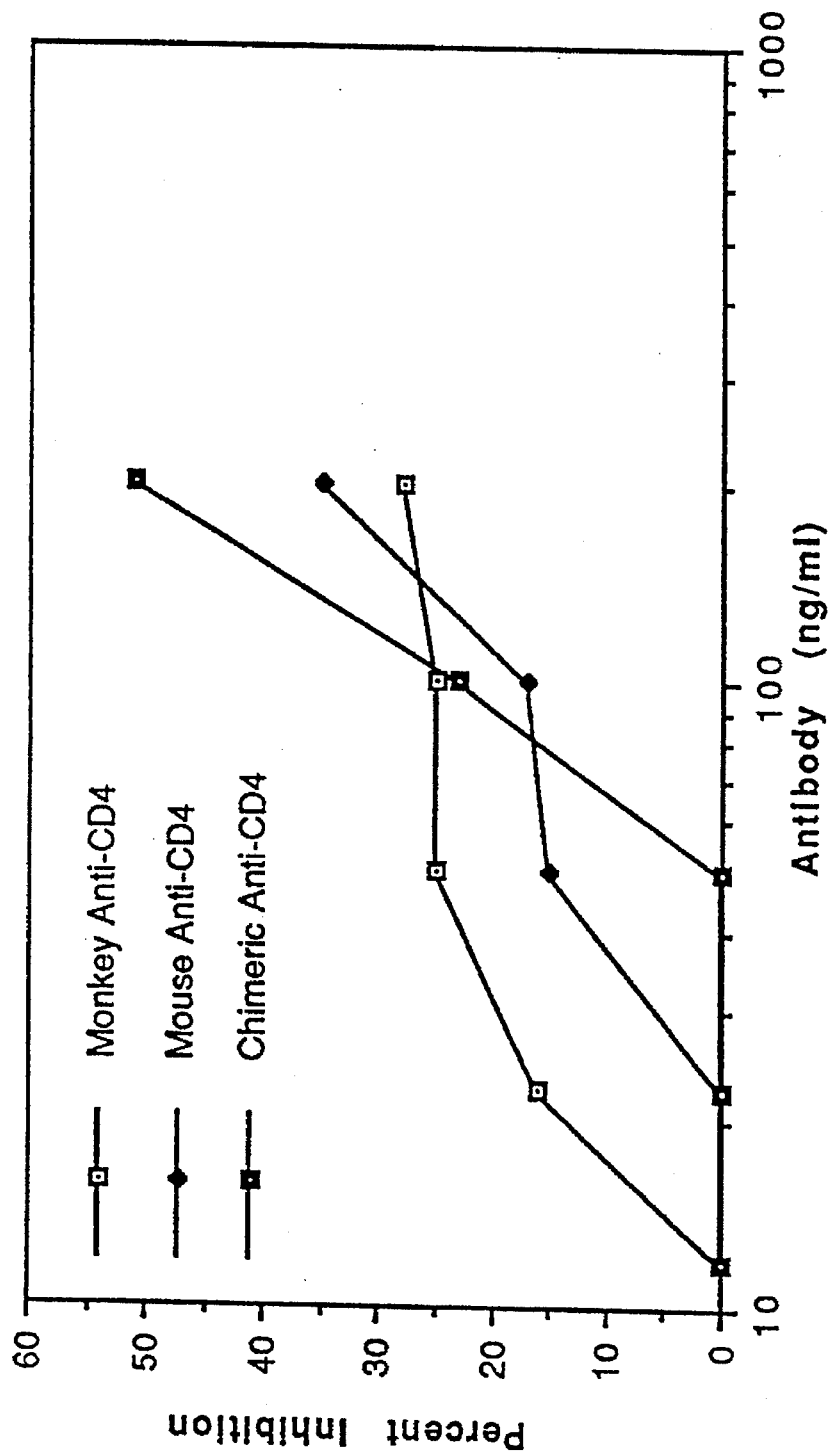
FIG. 12 is a graphical representation of the inhibition of binding of 1F3 by the antibody shown in FIG. 10.

The expression vector TCAE 5.2 and TCAE 6 are not only able to be used for stable integrated expression into the cell lines Sp2/0 and CHO but, because it includes the SV40 origin, is also able to be expressed transiently in the cell line COS. COS cell expression was performed as follows: COS cells were seeded one day before the transfection so that they would be 50–70% confluent the following day. Culture medium was removed and the cells washed twice with Transfection Buffer (TB—140 mM NaCl, 25 mM Tris, 5 mM KCl, 0.5 mM $Na_2HPO_4$ 1 mM $MgCl_2$, 1 mM $CaCl_2$). 30 µg of cesium chloride purified TCAE 6 plasmid containing the anti-CD4 monkey/human chimetic heavy and light immunoglobulin chains were mixed with 3 ml of DEAE dextran per dish (1 mg/ml in TB). The DNA was allowed to incubate with the cells for 1 hour at 37° C. DNA solution was removed and replaced with 3 ml of 20% glycerol for 1.5–2.5 minutes, after which the cells were twice washed with TB. Cells were incubated in 5 ml of fresh medium containing 100 uM chloroquine for 3–5 hours at 37° C., after which they were washed twice with medium and incubated with normal DMEM for 72 hours. Supernatant (100 µl) from the transfected COS cells was assayed at various dilutions for the presence of antibody by an ELISA-based technique. Goat anti-human lambda was used to coat 96 well assay plates and a peroxidase-labeled goat anti-human IgG as the detection antibody, under standard ELISA conditions. COS cells were found to produce between 10 and 40 ng/ml of monkey/human chimeric antibody. Larger volumes of supernatant were concentrated 10 fold and used in a direct binding RIA to CD4 positive supT1 cells. The parental whole monkey antibody and an irrelevant human immunoglobulin were used as a positive and negative controls respectively (FIG. 11). Furthermore, the monkey anti-CD4 and the monkey/human chimeric anti-CD4 were used to inhibit the binding of a high affinity mouse anti-CD4 (1F3) antibody (FIG. 12). It can be seen that the monkey/human recombinant antibody (ATCC No. 69030) not only binds to CD4 positive cells but is able to inhibit the binding of 1F3 to CD4 positive cells in approximately the same concentrations of wholly monkey antibody or 1F3 itself.

The following is an example of the methods and antibodies of this invention.

EXAMPLE 4

Generation of Monkey Antibodies Against Human Lymphocyte Antigens

Figure 15:
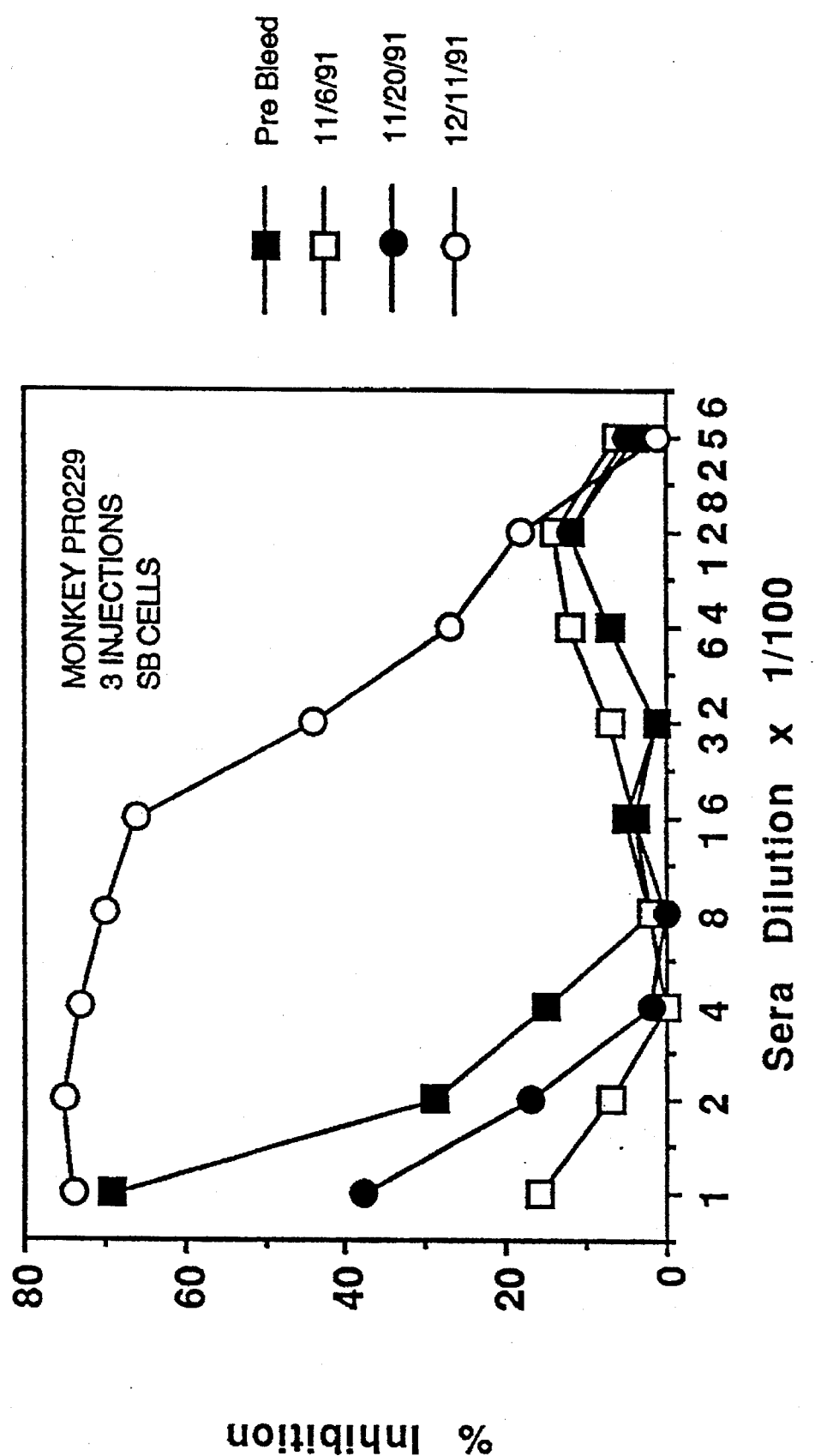
FIG. 15 is a graph showing anti-CD54 activity.

An adult cynomolgus monkey (White Sands New Mexico Primate Center) was immunized intramuscularly, at multiple sites, with $5 \times 10^8$ whole CD54 positive human lymphocytes. Cells used were alternately, SB cells (human B lymphoid line) and activated peripheral human lymphocytes, activated by pre-incubation with a mixture of pokeweed mitogen (2.5 mg/ml), phorbol monoacetate (40 nM) and phytohemagglutinin (4 mg/well) with the inclusion of a standard adjuvant. Immunization was repeated every 2–3 weeks over a period of 8 months. Sera from the immunized animals were screened at various times by inhibition of binding of a murine antibody, 84H10, known to bind to ICAM-1. A saturating amount of 84H10 was bound to chinese hamster ovary cells (CHO), previously transfected with an expression vector containing human CD54 c-DNA and selected for high expression of cell surface CD54, together with increasing dilutions of monkey serum. The inhibition of 84H10 binding is shown in FIG. 15.

Other murine monoclonal antibodies which recognize other human lymphocyte antigens were tested by inhibition using monkey sera obtained by the same immunization methods.

Use

Antibodies produced in the manner described above, or by equivalent techniques, can be purified by a combination of affinity and size exclusion chromatography for characterization in functional biological assays. These assays include determination of specificity and binding affinity as well as effector function associated with the expressed isotype, e.g., ADCC, or complement fixation. Such antibodies may be used as passive or active therapeutic agents against a number of human diseases, including B cell lymphoma, infectious diseases including AIDS, autoimmune and inflammatory diseases, and transplantation. The antibodies can be used either in their native form, or as part of an antibody/chelate, antibody/drug or antibody/toxin complex. Additionally, whole antibodies or antibody fragments (Fab$_2$, Fab, Fv) may be used as imaging reagents or as potential vaccines or immunogens in active immunotherapy for the generation of anti-idiotypic responses.

The amount of antibody useful to produce a therapeutic effect can be determined by standard techniques well known to those of ordinary skill in the art. The antibodies will generally be provided by standard technique within a pharmaceutically acceptable buffer, and may be administered by any desired route. Because of the efficacy of the presently claimed antibodies and their tolerance by humans it is possible to administer these antibodies repetitively in order to combat various diseases or disease states within a human.

The anti-CD4 recombinant antibodies (or fragments thereof) of this invention are also useful for inducing immunosuppression, i.e., inducing a suppression of a human's or animal's immune system. This invention therefore relates to a method of prophylactically or therapeutically inducing immunosuppression in a human or other animal in need thereof by administering an effective, non-toxic amount of such an antibody of this invention to such human or other animal.

The ability of the compounds of this invention to induce immunosuppression may be demonstrated in standard tests used for this purpose, for example, a mixed lymphocyte reaction test or a test measuring inhibition of T-cell proliferation measured by thymidine uptake.

The fact that the antibodies of this invention have utility in inducing immunosuppression means that they are useful in the treatment or prevention of resistance to or rejection of transplanted organs or tissues (e.g., kidney, heart, lung, bone marrow, skin, cornea, etc.); the treatment or prevention of autoimmune, inflammatory, proliferative and hyperproliferative diseases, and of cutaneous manifestations of immunologically medicated diseases (e.g., rheumatoid arthritis, lupus erythematosus, systemic lupus erythematosus, *Hashimotos thyroiditis*, multiple sclerosis, myasthenia gravis, type 1 diabetes, uveitis, nephrotic syndrome, psoriasis, atopical dermatitis, contact dermatitis and further eczematous dermatitides, seborrheic dermatitis, *Lichen planus*, Pemplugus, bullous pemphigus, *Epidermolysis bullosa*, urticaria, angioedemas, vasculitides, erythema, cutaneous eosinophilias, *Alopecia areata*, etc.); the treatment of reversible obstructive airways disease, intestinal inflammations and allergies (e.g., Coeliac disease, proctitis, eosinophilia gastroenteritis, mastocytosis, Crohn's disease and ulcerative colitis) and food-related allergies (e.g., migraine, rhinitis and eczema).

One skilled in the art would be able, by routine experimentation, to determine what an effective, non-toxic amount of antibody would be for the purpose of inducing immunosuppression. Generally, however, an effective dosage will be in the range of about 0.05 to 100 milligrams per kilogram body weight per day.

The antibodies (or fragments thereof) of this invention should also be useful for treating tumors in a mammal. More specifically, they should be useful for reducing tumor size, inhibiting tumor growth and/or prolonging the survival time of tumor-bearing animals. Accordingly, this invention also relates to a method of treating tumors in a human or other animal by administering to such human or animal an effective, non-toxic amount of an antibody. One skilled in the art would be able, by routine experimentation, to determine what an effective, non-toxic amount of antibody would be for the purpose of treating carcinogenic tumors. Generally, however, an effective dosage is expected to be in the range of about 0.05 to 100 milligrams per kilogram body weight per day.

The antibodies of the invention may be administered to a human or other animal in accordance with the aforementioned methods of treatment in an amount sufficient to produce such effect to a therapeutic or prophylactic degree. Such antibodies of the invention can be administered to such human or other animal in a conventional dosage form prepared by combining the antibody of the invention with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables.

The route of administration of the antibody (or fragment thereof) of the invention may be oral, parenteral, by inhalation or topical. The term parenteral as used herein includes intravenous, intramuscular, subcutaneous, rectal, vaginal or intraperitoneal administration. The subcutaneous and intramuscular forms of parenteral administration are generally preferred.

The daily parenteral and oral dosage regimens for employing compounds of the invention to prophylactically or therapeutically induce immunosuppression, or to therapeutically treat carcinogenic tumors will generally be in the range of about 0.05 to 100, but preferably about 0.5 to 10, milligrams per kilogram body weight per day.

The antibody of the invention may also be administered by inhalation. By "inhalation" is meant intranasal and oral inhalation administration. Appropriate dosage forms for such administration, such as an aerosol formulation or a metered dose inhaler, may be prepared by conventional techniques. The preferred dosage amount of a compound of the invention to be employed is generally within the range of about 10 to 100 milligrams.

The antibody of the invention may also be administered topically. By topical administration is meant non-systemic administration and includes the application of an antibody (or fragment thereof) compound of the invention externally to the epidermis, to the buccal cavity and instillation of such an antibody into the ear, eye and nose, and where it does not significantly enter the blood stream. By systemic administration is meant oral, intravenous, intraperitoneal and intramuscular administration. The amount of an antibody required for therapeutic or prophylactic effect will, of course, vary with the antibody chosen, the nature and severity of the condition being treated and the animal undergoing treatment, and is ultimately at the discretion of the physician. A suitable topical dose of an antibody of the invention will generally be within the range of about 1 to 100 milligrams per kilogram body weight daily.

Formulations

While it is possible for an antibody or fragment thereof to be administered alone, it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation.

The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 90°–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

It will be recognized by one of skill in the art that the optimal quantity and spacing of individual dosages of an antibody or fragment thereof of the invention will be determined by the nature and extent of the condition being treated, the form, route and site of administration, and the particular animal being treated, and that such optimums can be determined by conventional techniques. It will also be appreciated by one of skill in the art that the optimal course of treatment, i.e., the number of doses of an antibody or fragment thereof of the invention given per day for a defined number of days, can be ascertained by those skilled in the art using conventional course of treatment determination tests.

Without further elaboration, it is believed that one skilled in the art can, using the preceding description, utilize the present invention to its fullest extent. The following are, therefore, to be construed as merely illustrative examples and not a limitation of the scope of the present invention in any way.

Capsule Composition

A pharmaceutical composition of this invention in the form of a capsule is prepared by filling a standard two-piece hard gelatin capsule with 50 mg. of an antibody or fragment thereof of the invention, in powdered form, 100 mg. of lactose, 32 mg. of talc and 8 mg. of magnesium stearate.

Injectable Parenteral Composition

A pharmaceutical composition of this invention in a form suitable for administration by injection is prepared by stirring 1.5% by weight of an antibody or fragment thereof of the invention in 10% by volume propylene glycol and water. The solution is sterilized by filtration.

Ointment Composition

Antibody or fragment thereof of the invention 1.0 g.
White soft paraffin to 100.0 g.

The antibody or fragment thereof of the invention is dispersed in a small volume of the vehicle to produce a smooth, homogeneous product. Collapsible metal tubes are then filled with the dispersion.

Topical Cream Composition

Antibody or fragment thereof of the invention 1.0 g.
Polawax GP 200 20.0 g.
Lanolin Anhydrous 2.0 g.
White Beeswax 2.5 g.
Methyl hydroxybenzoate 0.1 g.
Distilled Water to 100.0 g.

The polawax, beeswax and lanolin are heated together at 60° C. A solution of methyl hydroxybenzoate is added and homogenization is achieved using high speed stirring. The temperature is then allowed to fall to 50° C. The antibody or fragment thereof of the invention is then added and dispersed throughout, and the composition is allowed to cool with slow speed stirring.

Topical Lotion Composition

Antibody or fragment thereof of the invention 1.0 g.
Sorbitan Monolaurate 0.6 g.
Polysorbate 20 0.6 g.
Cetostearyl Alcohol 1.2 g.
Glycerin 6.0 g.
Methyl Hydroxybenzoate 0.2 g.
Purified Water B.P. to 100.00 ml. (B.P.=British Pharmacopeia)

The methyl hydroxybenzoate and glycerin are dissolved in 70 ml. of the water at 75° C. The sorbitan monolaurate, polysorbate 20 and cetostearyl alcohol are melted together at 75° C. and added to the aqueous solution. The resulting emulsion is homogenized, allowed to cool with continuous stirring and the antibody or fragment thereof of the invention is added as a suspension in the remaining water. The whole suspension is stirred until homogenized.

Eye Drop Composition

Antibody or fragment thereof of the invention 0.5 g.
Methyl Hydroxybenzoate 0.01 g.
Propyl Hydroxybenzoate 0.04 g.
Purified Water B.P. to 100.00 ml.

The methyl and propyl hydroxybenzoates are dissolved in 70 ml. purified water at 75° C. and the resulting solution is allowed to cool. The antibody or fragment thereof of the invention is then added, and the solution is sterilized by filtration through a membrane filter (0.022 μm pore size), and packed aseptically into suitable sterile containers.

Composition for Administration by Inhalation

For an aerosol container with a capacity of 15–20 ml: mix 10 mg. of an antibody or fragment thereof of the invention with 0.2–0.5% of a lubricating agent, such as polysorbate 85 or oleic acid, and disperse such mixture in a propellant, such as freon, preferably in a combination of (1,2 dichlorotetrafluoroethane) and difluorochloromethane and put into an appropriate aerosol container adapted for either intranasal or oral inhalation administration.

Composition for Adminstration by Inhalation

For an aerosol container with a capacity of 15–20 ml: dissolve 10 mg. of an antibody or fragment thereof of the invention in ethanol (6–8 ml.), add 0.1–0.2% of a lubricating agent, such as polysorbate 85 or oleic acid; and disperse such in a propellant, such as freon, preferably in a combination of (1.2 dichlorotetrafluoroethane) and difluorochloromethane, and put into an appropriate aerosol container adapted for either intranasal or oral inhalation administration.

The antibodies and pharmaceutical compositions of the invention are particularly useful for parenteral administration, i.e., subcutaneously, intramuscularly or intravenously. The compositions for parenteral administration will commonly comprise a solution of an antibody or fragment thereof of the invention or a cocktail thereof dissolved in an acceptable carrier, preferably an aqueous carrier. A variety of aqueous carriers may be employed, e.g., water, buffered water, 0.4% saline, 0.3% glycine, and the like. These solutions are sterile and generally free of particulate matter. These solutions may be sterilized by conventional, well-known sterilization techniques. The compositions may contain pharmaceutically acceptable auxiliary substances as required to approximate physiological conditions such as pH adjusting and buffering agents, etc. The concentration of the antibody or fragment thereof of the invention in such pharmaceutical formulation can vary widely, i.e., from less than about 0.5%, usually at or at least about 1% to as much as 15 or 20% by weight, and will be selected primarily based on fluid volumes, viscosities, etc., according to the particular mode of administration selected.

Thus, a pharmaceutical composition of the invention for intramuscular injection could be prepared to contain 1 mL sterile buffered water, and 50 mg. of an antibody or fragment thereof of the invention. Similarly, a pharmaceutical composition of the invention for intravenous infusion could be made up to contain 250 ml. of sterile Ringer's solution, and 150 mg. of an antibody or fragment thereof of the invention. Actual methods for preparing parenterally administrable compositions are well-known or will be apparent to those skilled in the art, and are described in more detail in, for example, *Remington's pharmaceutical Science*, 15th ed., Mack Publishing Company, Easton, Pa., hereby incorporated by reference herein.

The antibodies (or fragments thereof) of the invention can be lyophilized for storage and reconstituted in a suitable carrier prior to use. This technique has been shown to be effective with conventional immune globulins and art-known lyophilization and reconstitution techniques can be employed.

Depending on the intended result, the pharmaceutical composition of the invention can be administered for prophylactic and/or therapeutic treatments. In therapeutic application, compositions are administered to a patient already suffering from a disease, in an amount sufficient to cure or at least partially arrest the disease and its complications. In prophylactic applications, compositions containing the present antibodies or a cocktail thereof are administered to a patient not already in a disease state to enhance the patient's resistance.

Single or multiple administrations of the pharmaceutical compositions can be carried out with dose levels and pattern being selected by the treating physician. In any event, the pharmaceutical composition of the invention should provide a quantity of the altered antibodies (or fragments thereof) of the invention sufficient to effectively treat the patient.

It should also be noted that the antibodies of this invention may be used for the design and synthesis of either peptide or non-peptide compounds (mimetics) which would be useful in the same therapy as the antibody. See, e.g., Saragovi et al., *Science*, 253, 792–795 (1991).

Deposit

To inventors' and their assignees acknowledge their responsibility to replace these cultures should they die before the end of the term of a patent issued hereon, 5 years after the last request for a culture, or 30 years, whichever is the longer, and its responsibility to notify the depository of the issuance of such a patent, at which time the deposit will be made irrevocably available to the public. Until that time the deposit will be made available to the Commissioner of Patents under the terms of 37 C.F.R. Section 1-14 and 35 U.S.C. Section 112.

Other embodiments are within the following claims.

We claim:

1. A chimeric antibody comprising an immunoglobulin constant region and an antigen binding region, said immunoglobulin constant region being selected from the group consisting of human immunoglobulin constant region and chimpanzee immunoglobulin constant region, and said antigen binding region being an Old World Monkey antigen-binding region.

2. A chimeric antibody conprising an immunoglobin variable region specific for a particular known antigen, said antibody comprising:
   (i) a constant region selected from the group consisting of human antibody constant region and chimpanzee antibody constant region;
   (ii) a framework region selected from the group consisting of human antibody framework region, chimpanzee antibody framework region and first Old World monkey antibody framework region; and
   (iii) a second Old World monkey antibody antigen binding portion.

3. The antibody of claim 1 or 2 wherein said antibody binds specifically to a human antigen.

4. The antibody of claim 1 or 2 wherein one said Old World monkey is a cynomolgus monkey.

5. The antibody of claim 1, wherein said antibody binds specifically to a human antigen.

6. The antibody of claim 1 or 2 wherein said antibody binds specifically to human antigens selected from the group consisting of CD58, VCAM, VDA4, CD2, LFA3, ELAM, LAM, CD25, CD4, CD19, CD20, CD23, CD41, CD44, CD54, TNFα, TNFβ, Tn antigen, IL-1, IL-8, human T-cell receptor, CD3, CD28, CD8, CD11a, CD11b, CD18, CD5a, CD11c, CD45, neu oncogene product, MDR-1, TGFα, TGFα receptor, PDGF, and CD71.

7. The antibody of claim 3 wherein said antibody binds specifically to human antigens selected from the group consisting of CD58, VCAM, VLA4, CD2, LFA3, ELAM, LAM, CD25, CD4, CD19, CD20, CD23, CD41, CD44, CD54, TNFα, TNFβ, Tn antigen, IL-1, IL-8, human T-cell receptor, CD3, CD28, CD8, CD11a, CD11b, CD11c, CD18, CD5a, CD45, neu oncogene product, MDR-1, TGFα, TGFα receptor, PDGF, and CD71.

8. The antibody of claim 4 wherein said antibody binds specifically to human antigens selected from the group consisting of CD58, VCAM, VLA4, CD2, LFA3, ELAM, LAM, CD23, CD25, CD4, CD19, CD20, CD41, CD44, CD54, TNFα, TNFβ, Tn antigen, IL-1, IL-8, human T-cell receptor, CD3, CD28, CD8, CD11a, CD11b, CD11c, CD18, CD5a, CD45, neu oncogene product, MDR-1, TGFα, TGFα receptor, PDGF, and CD71.

9. The antibody of claim 1 wherein each said Old World monkey is selected from the group consisting of baboon, Rhesus, and cynomolgus monkeys.

10. The antibody of claim 1 or 2 wherein said antigen-binding region comprises complementarity determining regions of an Old World monkey variable region.

11. The antibody of claim 1 or 2 wherein said antigen-binding portion comprises the whole variable region of an Old World monkey.

12. A method for producing a recombinant antibody to a human antigen, said antibody being not immunogenic in a human, comprising the steps of:
   a) raising an Old World monkey antibody to said antigen in an Old World monkey,
   b) isolating an Old World monkey nucleic acid encoding an antigen-binding region of a variable region of said Old World monkey antibody,
   c) providing a human nucleic acid encoding a human constant region of a human antibody,
   d) ligating said Old World monkey nucleic acid and said human nucleic acid to form a recombinant nucleic acid, and
   e) expressing said recombinant nucleic acid to produce said recombinant antibody.

13. The method of claim 12 wherein said antigen-binding region comprises complementarity determining regions of an Old World monkey variable region.

14. The method of claim 12 wherein said antigen-binding region comprises the whole variable region of an Old World monkey.

15. The method of claim 12, wherein before b) and after a) said method further comprises the step of immortalizing a cell able to produce said Old World monkey antibody.

16. The method of claim 12, further comprising the step of ascertaining whether said recombinant antibody binds to said human antigen.

17. The method of claim 15 wherein said immortalizing is by hybridoma fusion.

18. The method of claim 15 wherein said immortalizing is by viral transformation.

19. The method of claim 15 wherein said immortalizing is by single B-cell cloning.

20. The method of claim 15 wherein said recombinant antibody is produced in a library which is capable of expressing recombinant immunoglobulins.

21. The method of claim 15 wherein said human constant region is selected to have a desired isotype.

22. The method of claim 15 wherein before b) and after a) said method further comprises selecting a B-cell from said Old World monkey wherein said B-cell expresses said Old World Monkey antibody.

23. The method of claim 22 wherein said B-cell is obtained from peripheral blood lymphocytes, lymph node, bone marrow or spleen.

24. The method of claim 12 wherein before b) and after a) said method further comprises screening cells of said Old World monkey for production of said Old World Monkey antibody.

25. The method of claim 12 wherein said expressing is within a producer cell line.

26. The method of claim 12 wherein said isolating comprises immunoglobulin gene rescue of said variable region.

27. The method of any of claims 12–19, wherein said antigen is selected from the group consisting of CD58, VCAM, VLA4, CD2, LFA3, ELAM, LAM, CD25, CD4, CD19, CD20, CD23, CD41, CD44, CD54, TNFα, TNFβ, Tn antigen, IL-1, IL-8, human T-cell receptor, CD3, CD28, CD8, CD18, CD11a, CD11b, CD11c, C5a, CD45, neu oncogene product, MDR-1, TGFα, TGFα receptor, PDGF, and CD71.

28. A recombinant antibody comprising
   (1) a constant region of a heavy chain of a human antibody;
   (2) a constant region of a light chain of said human antibody;
   (3) a variable region of a heavy chain of an Old World monkey antibody specific for a human antigen; and
   (4) a variable region of a light chain of said Old World monkey antibody.

29. A composition comprising an antibody of any of claims 1 or 2 in an acceptable carrier.

30. The composition of claim 29 where said antibody binds specifically to CD58, VCAM, VLA4, CD2, LFA3, ELAM, LAM, CD25, CD4, CD19, CD20, CD23, CD41, CD44, CD54, TNFα, TNFβ, Tn antigen, IL-1, IL-8, human T-cell receptor, CD3, CD28, CD8, CD18, CD11a, CD11b, CD11c, C5a, CD45, neu oncogene product, MDR-1, TGFα, TGFα receptor, PDGF, or CD71.

31. The antibody of claim 2 wherein said first Old World monkey and said second Old World monkey are different monkeys.

32. The antibody of claim 2 wherein said first Old World monkey and said second Old World monkey are the same monkey.

33. An anti-CD4 antibody which comprises the variable light and variable heavy regions encoded by the DNA sequences set forth in SEQ ID NO: 20 and SEQ ID NO: 19.

34. The antibody of claim 33, wherein said antibody is a chimeric recombinant antibody which contains a constant region selected from the group consisting of human constant regions and Old World monkey constant regions which is from a different Old World Monkey antibody that is used to obtain said variable light and variable heavy regions.

35. The chimeric recombinant antibody of claim 34, wherein said human constant regions are selected from the group consisting of human gamma 1, human Kappa and human lambda.

36. The chimeric recombinant antibody of claim 35, wherein the antibody is produced by ATCC Accession No. 69030.

37. The antibody of claim 2 wherein one said Old World monkey is a Rhesus monkey.

38. The method of claim 12 wherein said recombinant antibody is expressed using a vector comprising a selectable marker gene containing an altered translation initiation sequence which results in impaired translation initiation relative to a selectable marker gene which does not contain said altered translation initiation sequence.

* * * * *

UNITED STATES PATENT AND TRADEMARK OFFICE
CERTIFICATE OF CORRECTION

PATENT NO. : 5,658,570
DATED : August 19, 1997
INVENTOR(S) : Newman et al

It is certified that error appears in the above-identified patent and that said Letters Patent is hereby corrected as shown below:

COL. 35   line 49, delete "VDA4" and replace with --VLA4--.

Signed and Sealed this

Twenty-seventh Day of March, 2001

Attest:

NICHOLAS P. GODICI

Attesting Officer   Acting Director of the United States Patent and Trademark Office

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

CAGAGCTGGG TACGTCCTCA    20

( 2 ) INFORMATION FOR SEQ ID NO:2:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:2:

GCCCCAGAG GTGCTCTTGG                      20

( 2 ) INFORMATION FOR SEQ ID NO:3:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:3:

CAGAGCTGGG TACGTGAACC                      20

( 2 ) INFORMATION FOR SEQ ID NO:4:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:4:

GGCTTGAAGC TCCTCAGAGG                      20

( 2 ) INFORMATION FOR SEQ ID NO:5:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:5:

CCATGGACTG GACCTGG                        17

( 2 ) INFORMATION FOR SEQ ID NO:6:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:6:

ATGGACATAC TTTGTTCCAC                      20

( 2 ) INFORMATION FOR SEQ ID NO:7:

( i ) SEQUENCE CHARACTERISTICS:
    ( A ) LENGTH: 20 base pairs ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:7:

CCATGGAGTT TGGGCTGAGC                                                                      20

( 2 ) INFORMATION FOR SEQ ID NO:8:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:8:

ATGAAACACC TGTGGTTCTT                                                                      20

( 2 ) INFORMATION FOR SEQ ID NO:9:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:9:

ATGGGGTCAA CCGCCATCCT                                                                      20

( 2 ) INFORMATION FOR SEQ ID NO:10:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:10:

ATGTCTGTCT CCTTCCTCAT                                                                      20

( 2 ) INFORMATION FOR SEQ ID NO:11:

( i ) SEQUENCE CHARACTERISTICS:
          ( A ) LENGTH: 16 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:11:

TTGGGGCGGA TGCACT                                                                          16

( 2 ) INFORMATION FOR SEQ ID NO:12:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:12:

GATGGGCCCT TGGTGGA                                                                17

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 17
        ( D ) OTHER INFORMATION: /note= "Nucleotide 17 wherein N is
            G or T."

( x i ) SEQUENCE DESCRIPTION: SEQ ID NO:13:

GATGACCCAG TCTCCANCCT C                                                           21

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 5
        ( D ) OTHER INFORMATION: /note= "Nucleotide 5 wherein N is C
            or T."

( i x ) FEATURE:
        ( A ) NAME/KEY: misc_feature
        ( B ) LOCATION: 7
        ( D ) OTHER INFORMATION: /note= "Nucleotide 7 wherein N is T
            or C."

( i x ) FEATURE:
        ( A ) NAME/KEY: misc_feature
        ( B ) LOCATION: 8
        ( D ) OTHER INFORMATION: /note= "Nucleotide 8 wherein N is G
            or A."

( i x ) FEATURE:
        ( A ) NAME/KEY: misc_feature
        ( B ) LOCATION: 13
        ( D ) OTHER INFORMATION: /note= "Nucleotide 13 wherein N is
            A or C."

( x i ) SEQUENCE DESCRIPTION: SEQ ID NO:14:

CTCANTNNCT GCNCAGGGTC C                                                           21

( 2 ) INFORMATION FOR SEQ ID NO:15:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

AAGACAGATG GTGCAGCCA                                                              19

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
GGAACAGAGT GACCGAGGGG                                                      20
```

( 2 ) INFORMATION FOR SEQ ID NO:17:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

```
ACTAAGTCGA CATGAAACAC CTGTGGTTCT T                                         31
```

( 2 ) INFORMATION FOR SEQ ID NO:18:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

```
ATCACAGATC TCTCACCATG ACCTGCTCCC CTCTCCTCC                                 39
```

( 2 ) INFORMATION FOR SEQ ID NO:19:

( i ) SEQUENCE CHARACTERISTICS:
        ( A ) LENGTH: 423 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

```
GACATGAAAC ACCTGTGGTT CTTCCTCCTC CTGGTGGCAG CCCCCAGATG GGTCTTGTCC          60
CAGGTGCAGC TGCAGGAGGC GGGCCCAGGA CTGGTGAAGC CTTCGGAGAC CCTGTCCCTC         120
ACCTGCAGTG TCTCTGGTGG CTCCATCAGC GGTGACTATT ATTGGTTCTG GATCCGCCAG         180
TCCCCAGGGA AGGGACTGGA GTGGATCGGC TACATCTATG GCAGTGGTGG GGGCACCAAT         240
TACAATCCCT CCCTCAACAA TCGAGTCTCC ATTTCAATAG ACACGTCCAA GAACCTCTTC         300
TCCCTGAAAC TGAGGTCTGT GACCGCCGCG GACACGGCCG TCTATTACTG TGCGAGTAAT         360
ATATTGAAAT ATCTTCACTG GTTATTATAC TGGGGCCAGG GAGTCCTGGT CACCGTCTCC         420
TCA                                                                      423
```

( 2 ) INFORMATION FOR SEQ ID NO:20:

( i ) SEQUENCE CHARACTERISTICS:
        ( A ) LENGTH: 387 base pairs
        ( B ) TYPE: nucleic acid -continued (C) STRANDEDNESS: single
(D) TOPOLOGY: linear (ii) MOLECULE TYPE: DNA (genomic)

(xi) SEQUENCE DESCRIPTION: SEQ ID NO:20:

```
ACCATGGCCT GGGCTCTGCT GCTCCTCGGC CTCCTTGCTC ACTTTACAGA CTCTGCGGCC        60

TCCTATGAGT TGAGTCAGCC TCGCTCAGTG TCCGTGTCCC CAGGACAGAC GGCCGGGTTC       120

ACCTGTGGGG GAGACAACGT TGGAAGGAAA AGTGTACAGT GGTACCAGCA GAAGCCACCG       180

CAGGCCCCTG TGCTGGTCAT CTATGCTGAC AGCGAACGGC CCTCAGGGAT CCCTGCGCGA       240

TTCTCTGGCT CCAACTCAGG GAACACCGCC ACCCTGACCA TCAGCGGGGT CGAGGCCGGG       300

GATGAGGCTG ACTATTACTG TCAGGTGTGG GACAGTACTG CTGATCATTG GGTCTTCGGC       360

GGAGGGACCC GGCTGACCGT CCTAGGT                                          387
```